(12) United States Patent
Fong et al.

(10) Patent No.: US 7,671,026 B2
(45) Date of Patent: Mar. 2, 2010

(54) CYTOMODULATING PEPTIDES FOR TREATING INTERSTITIAL CYSTITIS

(75) Inventors: Timothy Fong, Moraga, CA (US); Alexis E. Te, Manhasset, NY (US)

(73) Assignee: Sangstat Medical Corporation, Fremont, CA (US)

(*) Notice: Subject to any disclaimer, the term of this patent is extended or adjusted under 35 U.S.C. 154(b) by 821 days.

(21) Appl. No.: 10/535,167

(22) PCT Filed: Nov. 17, 2003

(86) PCT No.: PCT/US03/37043
§ 371 (c)(1),
(2), (4) Date: Apr. 10, 2006

(87) PCT Pub. No.: WO2004/045554
PCT Pub. Date: Jun. 3, 2004

(65) Prior Publication Data
US 2006/0194738 A1    Aug. 31, 2006

Related U.S. Application Data

(60) Provisional application No. 60/426,684, filed on Nov. 15, 2002, provisional application No. 60/470,839, filed on May 15, 2003.

(51) Int. Cl.
*A61K 38/08* (2006.01)
*A61K 38/02* (2006.01)

(52) U.S. Cl. .................................. 514/15; 514/2
(58) Field of Classification Search .................. None
See application file for complete search history.

(56) References Cited

U.S. PATENT DOCUMENTS

| 6,696,545 B1 * | 2/2004 | Buelow et al. | 530/328 |
| 7,026,296 B2 * | 4/2006 | Gamache | 514/16 |
| 2001/0000783 A1 * | 5/2001 | Keay et al. | 514/2 |

FOREIGN PATENT DOCUMENTS

WO    WO 98/46633 A1 * 10/1998

OTHER PUBLICATIONS

Gonzalez et al. RDP58 Reduces Bladder Inflammation In A Murine Model Of Acute Inflammatory Cystitis. Journal of Urology. Apr. 27, 2003, vol. 169, No. 4, Supplement, pp. 68-69, Abstract No. 264.*

* cited by examiner

*Primary Examiner*—Jeffrey E Russel
(74) *Attorney, Agent, or Firm*—Todd Lorenz

(57) ABSTRACT

The methods and compositions relate to treatment of disorders of the bladder. In particular, the methods provide for treatment of interstitial cystitis and related disorders. The methods further comprise treatment to affect various manifestations associated with interstitial cystitis, including, reducing histamine release, modulating Substance P expression, modulating nerve growth factor expression, modulating levels of various cytokines, and maintaining integrity of the urine/blood barrier.

16 Claims, 16 Drawing Sheets

FIG._1

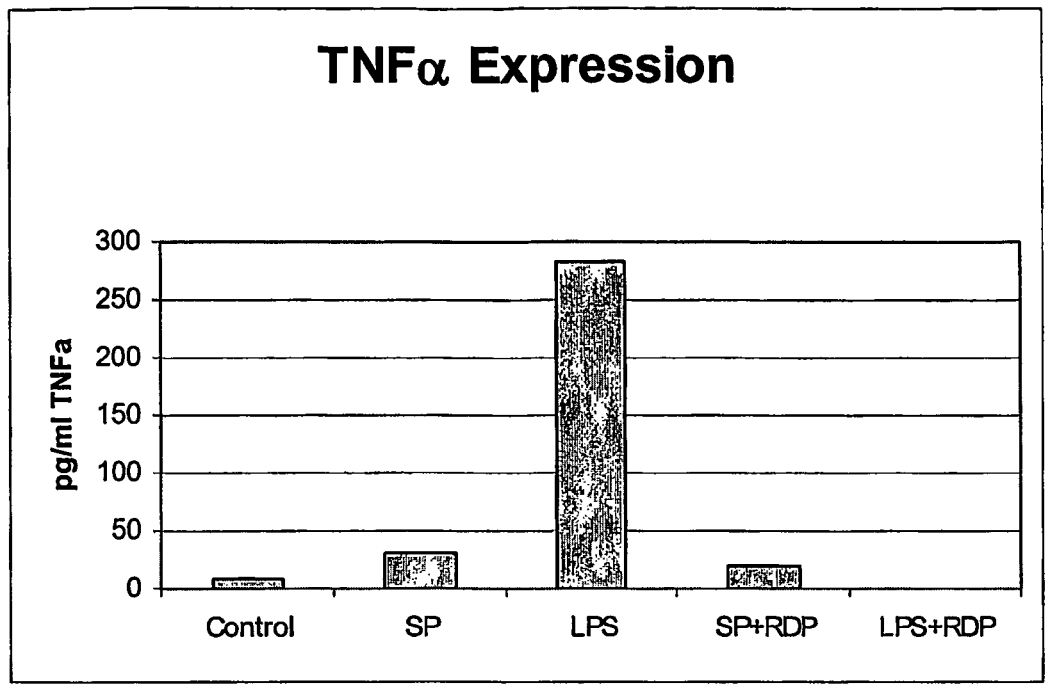
FIG._3A
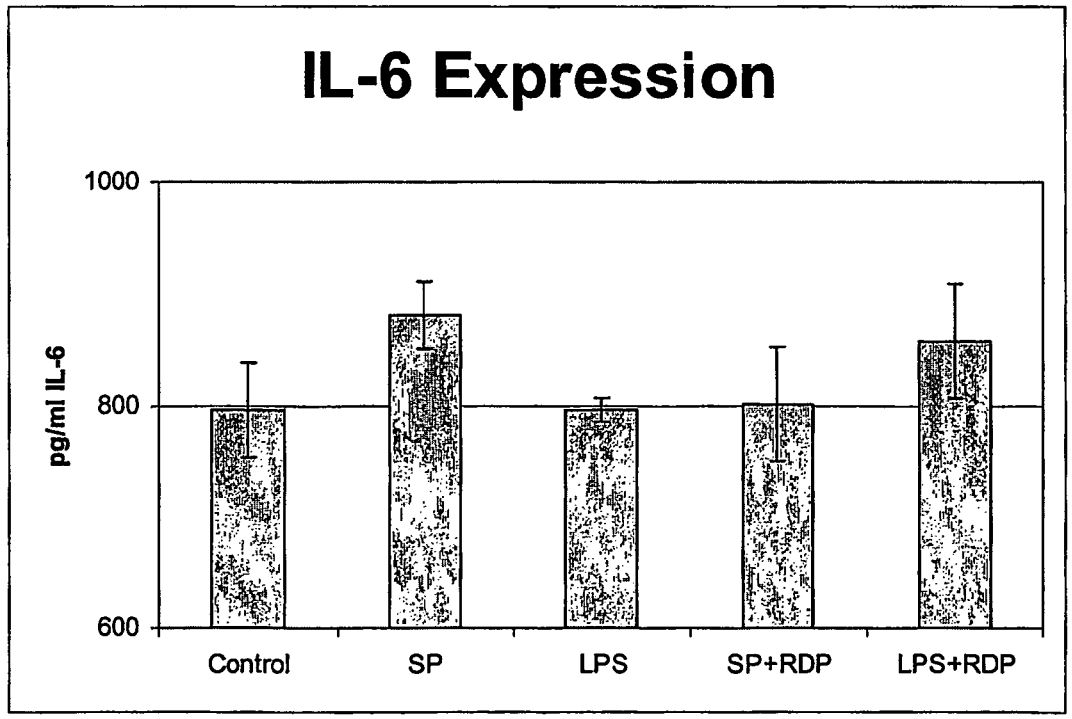
FIG._3B

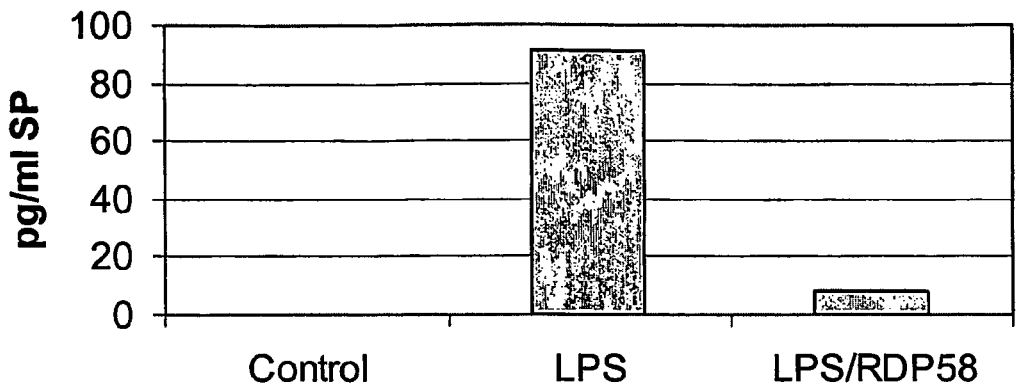
FIG._3C
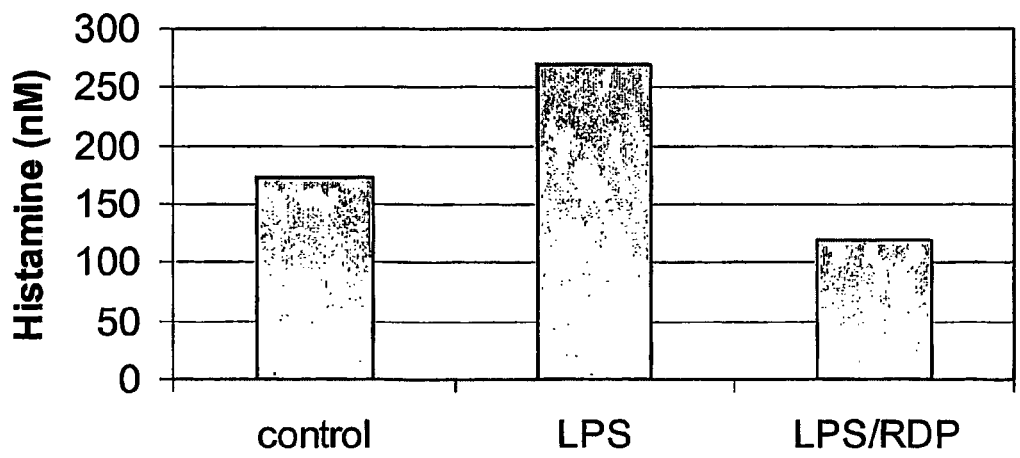
FIG._3D

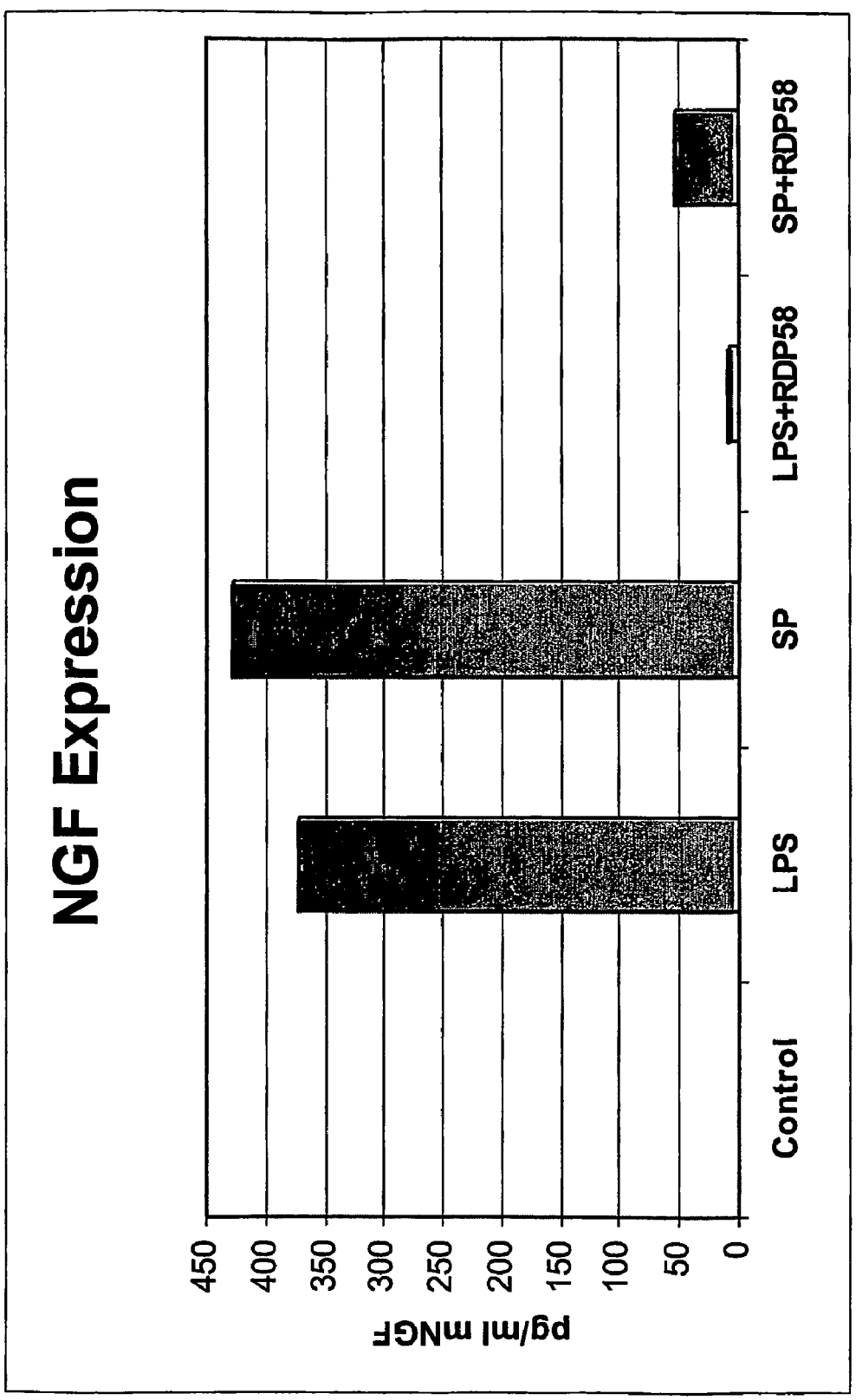
FIG._3E

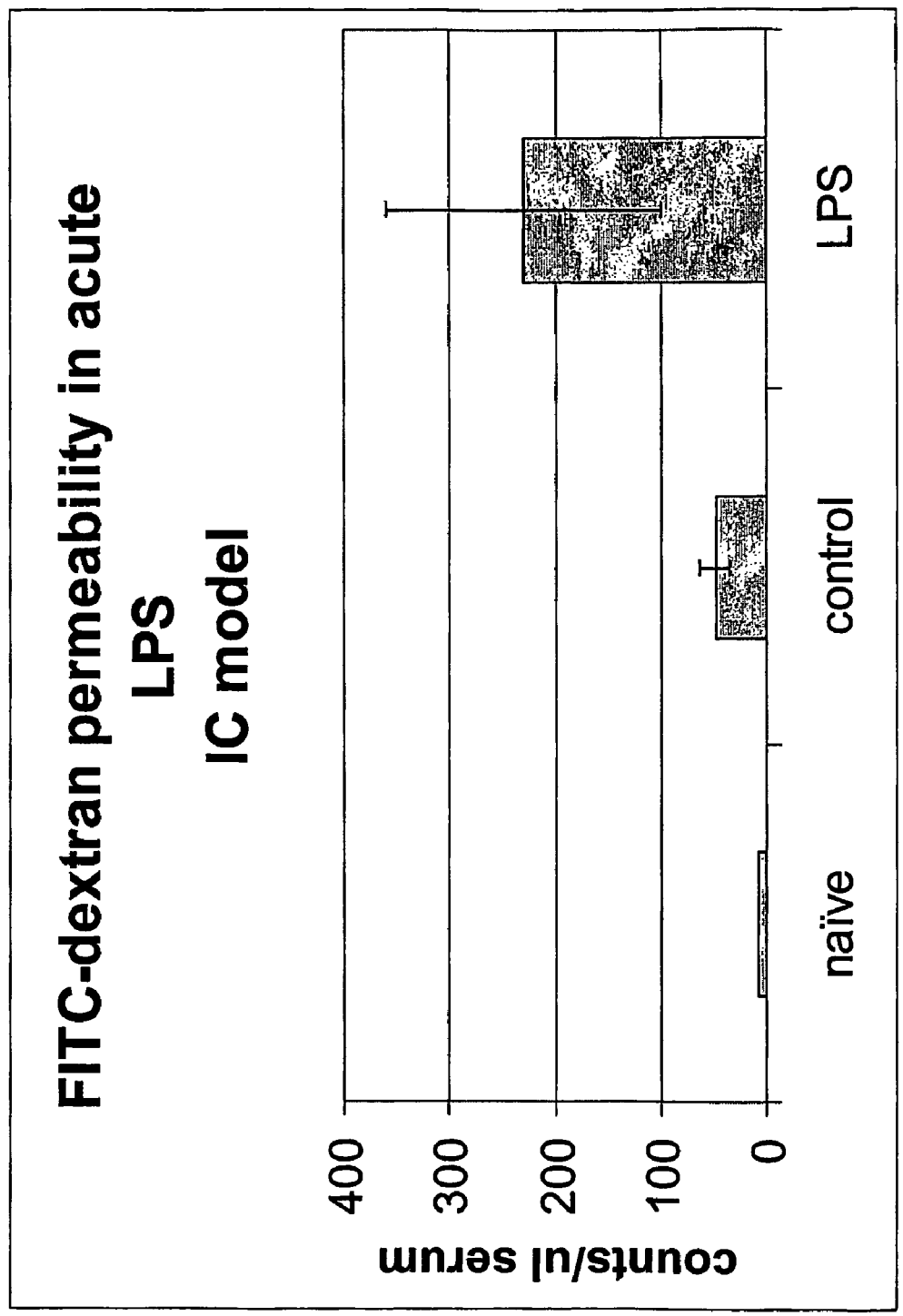
FIG._4

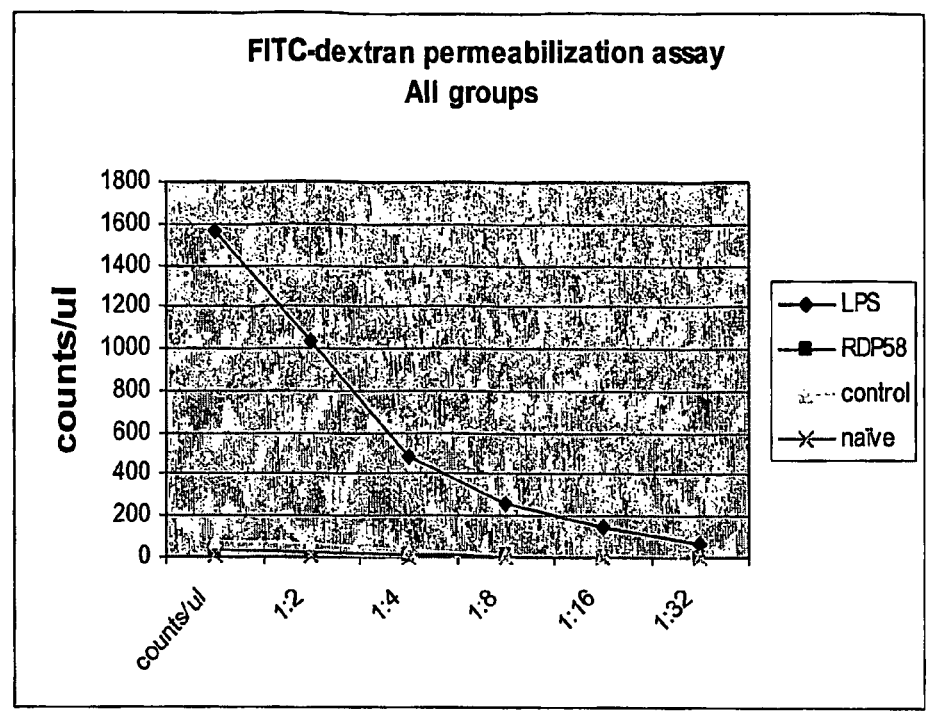
FIG._5A
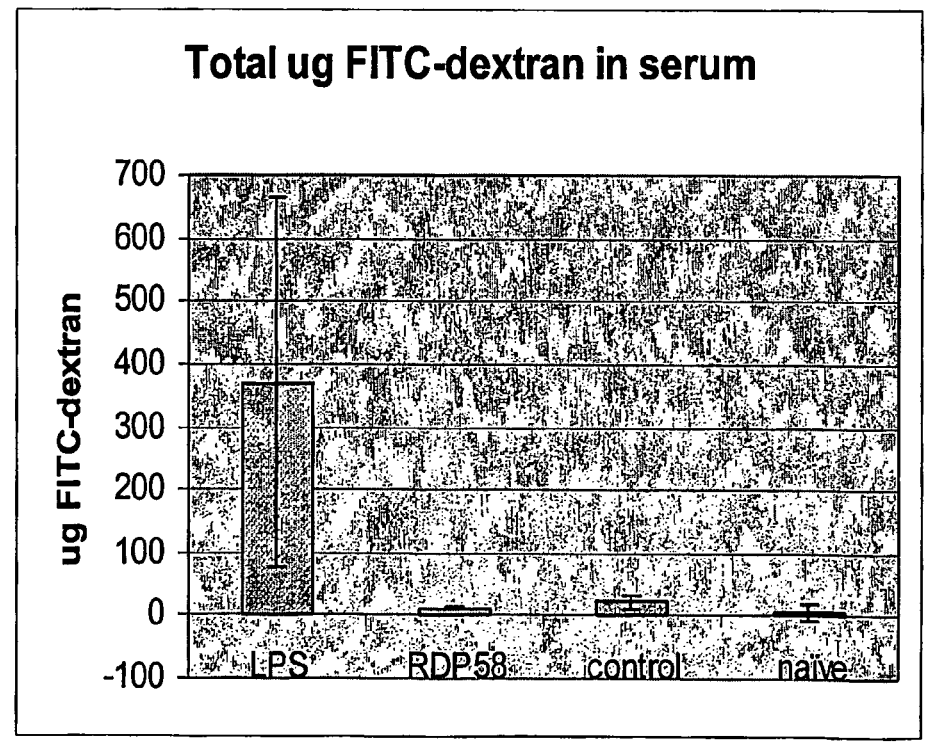
FIG._5B

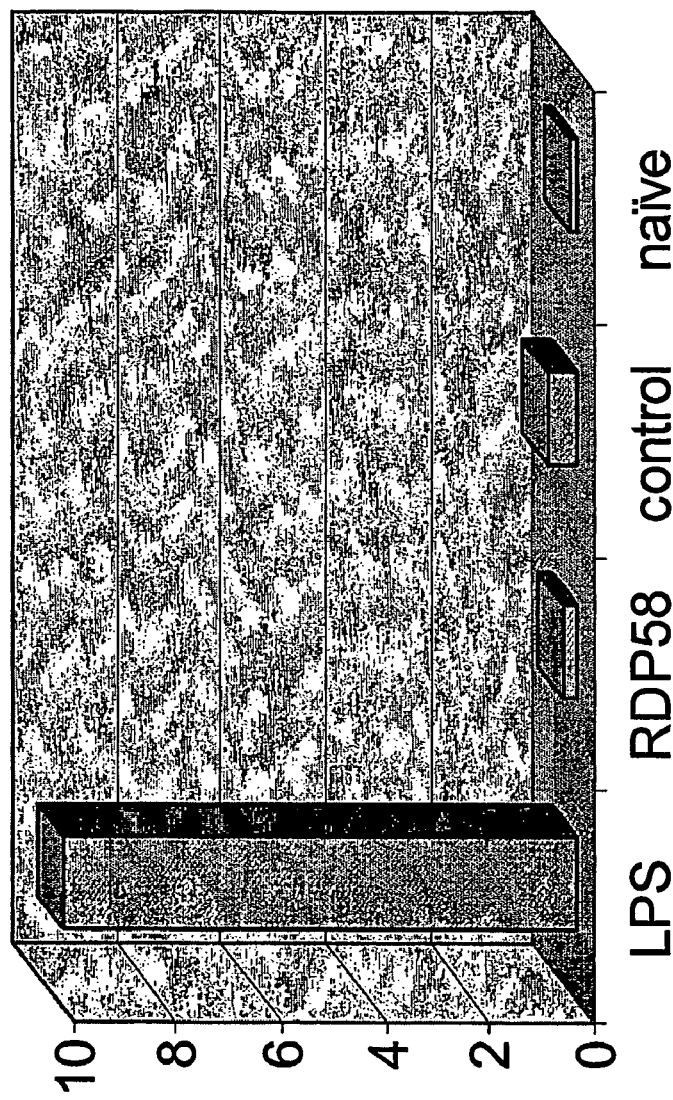
FIG._6

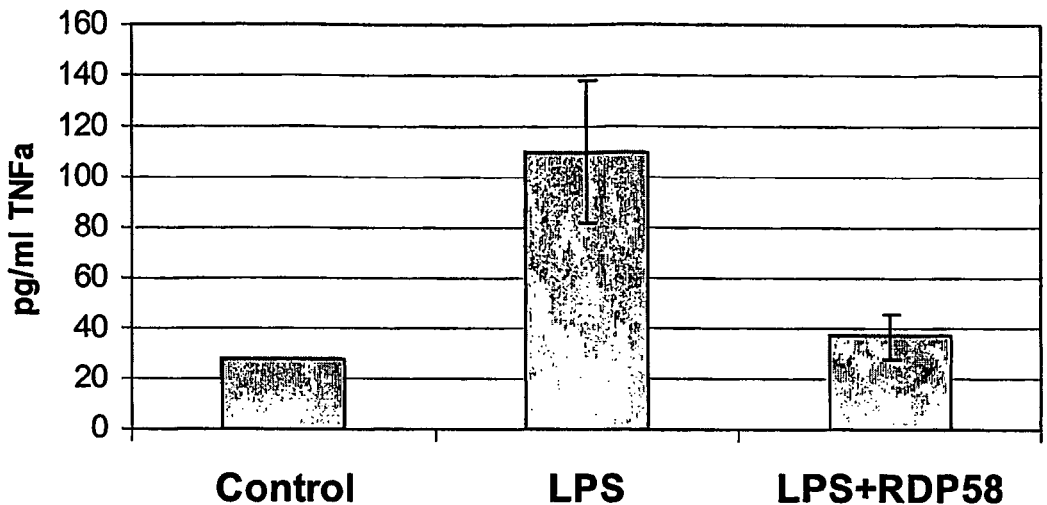
*FIG._7A*
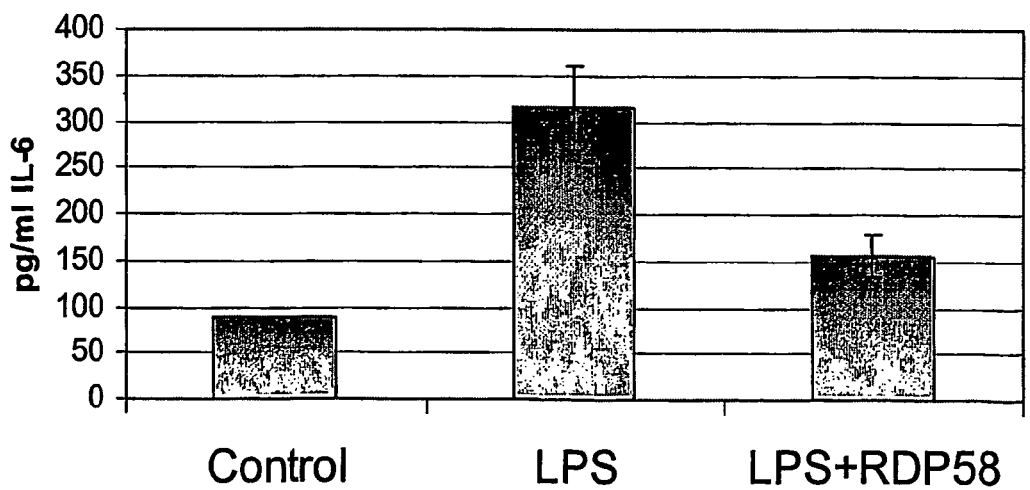
*FIG._7B*

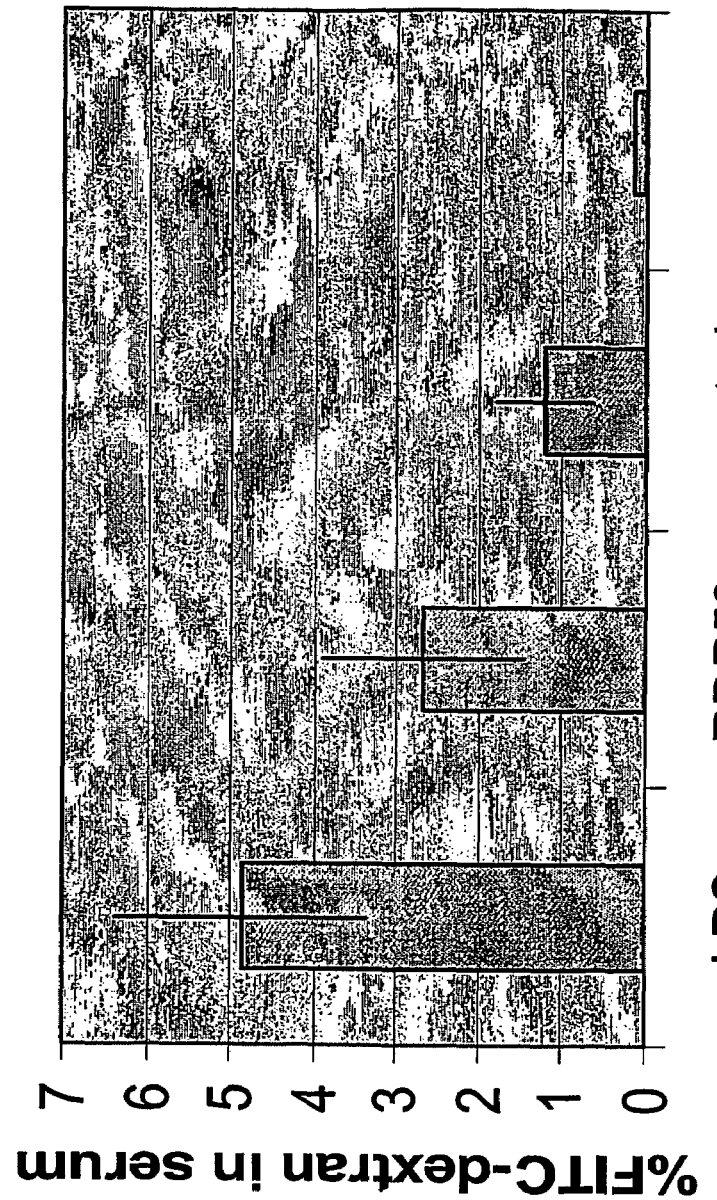
FIG._8

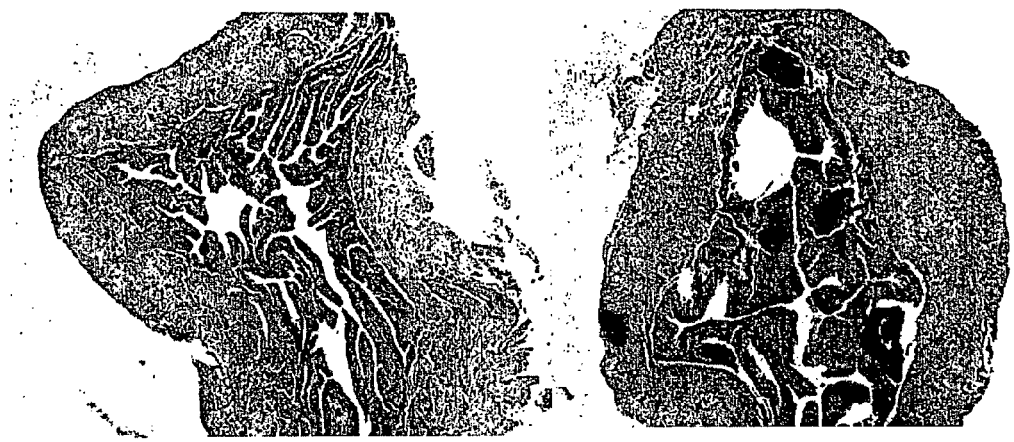
FIG._9A  FIG._9B
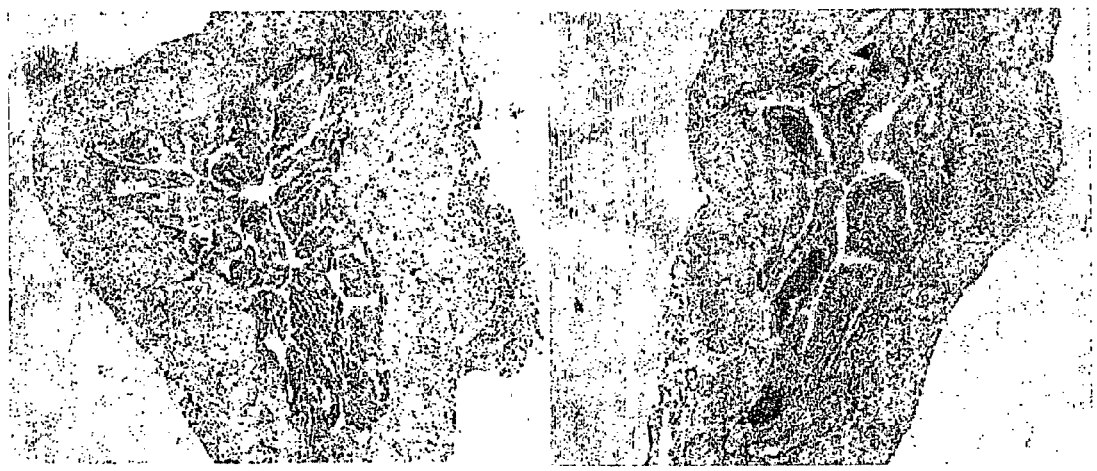
FIG._9C  FIG._9D

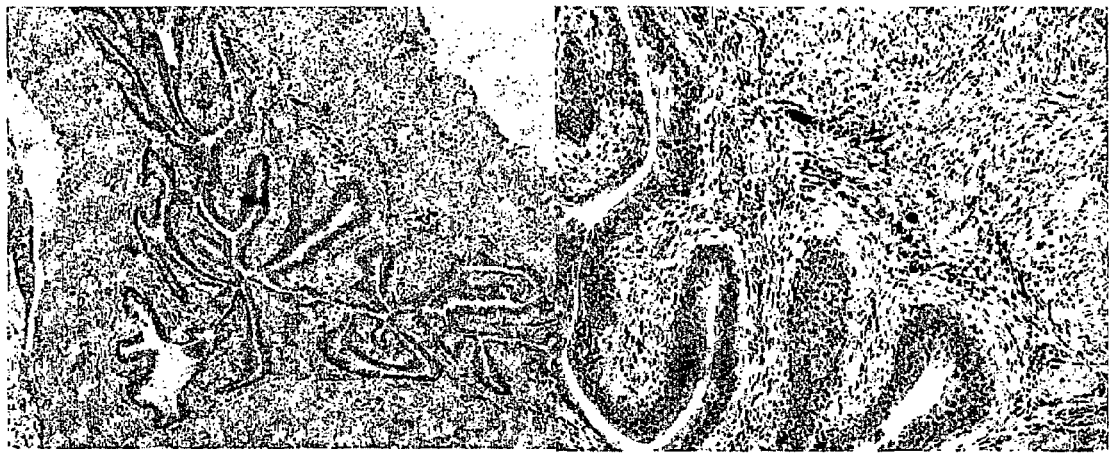
*FIG._10A*  *FIG._10B*
*FIG._10C*  *FIG._10D*

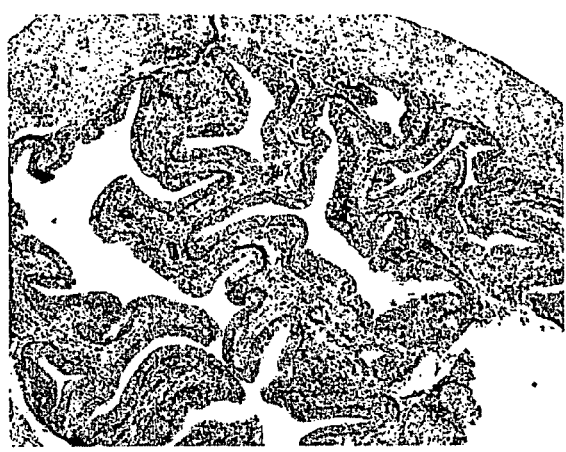 
FIG._10E                    FIG._10F

 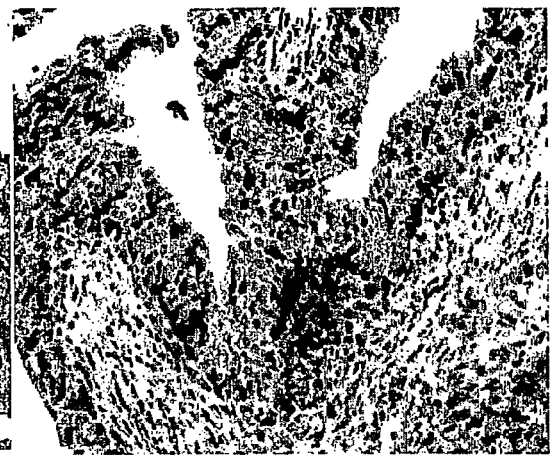
*FIG._11A*   *FIG._11B*
 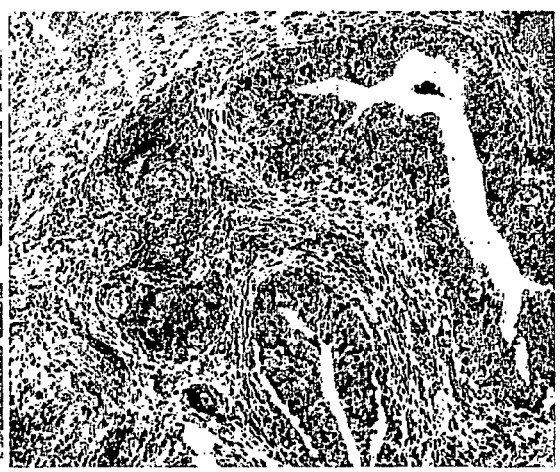
*FIG._11C*   *FIG._11D*

*FIG._11E*  *FIG._11F*
*FIG._11G*  *FIG._11H*

FIG._12A　　　　　　　　　FIG._12B
FIG._12C　　　　　　　　　FIG._12D

```
                       SEQUENCE LISTING

<160> NUMBER OF SEQ ID NOS: 40

<210> SEQ ID NO 1
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = any basic amino acid, preferably lys or
      arg
<220> FEATURE:
<221> NAME/KEY: MISC_FEATURE
<222> LOCATION: (2)..(4)
<223> OTHER INFORMATION: Xaa = an aliphatic or aromatic amino acid,
      e.g., a non-polar aliphatic amino acid, preferably of from 5 to 6
      carbons
<220> FEATURE:
<221> NAME/KEY: MISC_FEATURE
<222> LOCATION: (5)..(5)
<223> OTHER INFORMATION: Xaa = any basic amino acid, preferably lys or
      arg
<220> FEATURE:
<221> NAME/KEY: MISC_FEATURE
<222> LOCATION: (6)..(8)
<223> OTHER INFORMATION: Xaa = an aliphatic or aromatic amino acid,
      e.g., a non-polar aliphatic amino acid, preferably of from 5 to 6
      carbons
<220> FEATURE:
<221> NAME/KEY: MISC_FEATURE
<222> LOCATION: (9)..(9)
<223> OTHER INFORMATION: Xaa = gly or any basic amino acid or an
      aliphatic hydrophobic amino acid of from 5-6 carbon atoms

<400> SEQUENCE: 1

Xaa Xaa Xaa Xaa Xaa Xaa Xaa Xaa Xaa Tyr
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Xaa = an uncharged aliphatic or aromatic amino
      acid, preferably a non-polar aliphatic or aromatic amino acid
<220> FEATURE:
<221> NAME/KEY: MISC_FEATURE
<222> LOCATION: (3)..(4)
<223> OTHER INFORMATION: Xaa = an aliphatic or aromatic amino acid,
      e.g., a non-polar aliphatic amino acid, preferably of from 5 to 6
      carbons
<220> FEATURE:
<221> NAME/KEY: MISC_FEATURE
<222> LOCATION: (6)..(8)
<223> OTHER INFORMATION: Xaa = an aliphatic or aromatic amino acid,
      e.g., a non-polar aliphatic amino acid,preferably of from 5 to 6
      carbons
<220> FEATURE:
<221> NAME/KEY: MISC_FEATURE
<222> LOCATION: (9)..(9)
<223> OTHER INFORMATION: Xaa = gly, or any basic amino acid, or an
      aliphatic hydrophobic amino acid of from 5-6 carbon atoms

<400> SEQUENCE: 2

Arg Xaa Xaa Xaa Arg Xaa Xaa Xaa Xaa Tyr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Arg Leu Leu Leu Arg Leu Leu Leu Gly Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Arg Val Leu Leu Arg Leu Leu Leu Gly Tyr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Arg Ile Leu Leu Arg Leu Leu Leu Gly Tyr
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Arg Leu Val Leu Arg Leu Leu Leu Gly Tyr
1               5                   10
```

```
<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Arg Leu Ile Leu Arg Leu Leu Leu Gly Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic

<400> SEQUENCE: 8

Arg Leu Leu Val Arg Leu Leu Leu Gly Tyr
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Arg Leu Leu Ile Arg Leu Leu Leu Gly Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Arg Leu Leu Leu Arg Val Leu Leu Gly Tyr
1               5                   10

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Arg Leu Leu Leu Arg Ile Leu Leu Gly Tyr
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Arg Leu Leu Leu Arg Leu Val Leu Gly Tyr
1               5                   10
```

```
<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Arg Leu Leu Leu Arg Leu Ile Leu Gly Tyr
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Synthetic

<400> SEQUENCE: 14

Arg Leu Leu Leu Arg Leu Leu Val Gly Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Arg Leu Leu Leu Arg Leu Leu Ile Gly Tyr
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Arg Trp Leu Leu Arg Leu Leu Leu Gly Tyr
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Arg Leu Trp Leu Arg Leu Leu Leu Gly Tyr
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Arg Leu Leu Trp Arg Leu Leu Leu Gly Tyr
1               5                   10
```

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Arg Leu Leu Leu Arg Trp Leu Leu Gly Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Arg Leu Leu Leu Arg Leu Trp Leu Gly Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic

<400> SEQUENCE: 21

Arg Leu Leu Leu Arg Leu Leu Trp Gly Tyr
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Arg Tyr Leu Leu Arg Leu Leu Leu Gly Tyr
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Arg Leu Tyr Leu Arg Leu Leu Leu Gly Tyr
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Arg Leu Leu Tyr Arg Leu Leu Leu Gly Tyr
1               5                   10

```
<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Arg Leu Leu Leu Arg Tyr Leu Leu Gly Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthetic

<400> SEQUENCE: 26

Arg Leu Leu Leu Arg Leu Tyr Leu Gly Tyr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Synthetic

<400> SEQUENCE: 27

Arg Leu Leu Leu Arg Leu Leu Tyr Gly Tyr
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = norleucine
<220> FEATURE:
<221> NAME/KEY: MISC_FEATURE
<222> LOCATION: (6)..(8)
<223> OTHER INFORMATION: Xaa = norleucine

<400> SEQUENCE: 28

Arg Xaa Xaa Xaa Arg Xaa Xaa Xaa Gly Tyr
1               5                   10

<210> SEQ ID NO 29
<211> LENGTH: 5
<212> TYPE: PRT
<213> ORGANISM: Artificial Sequence
<220> FEATURE:
<223> OTHER INFORMATION: Synthetic

<400> SEQUENCE: 29

Gly Ser Gly Gly Ser
1               5

<210> SEQ ID NO 30
<211> LENGTH: 4
<212> TYPE: PRT
<213> ORGANISM: Artificial Sequence
<220> FEATURE:
<223> OTHER INFORMATION: Synthetic
```

-continued

```
<400> SEQUENCE: 30

Gly Gly Gly Ser
1

<210> SEQ ID NO 31
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: Xaa = any amino acid
<220> FEATURE:
<221> NAME/KEY: MISC_FEATURE
<222> LOCATION: (7)..(9)
<223> OTHER INFORMATION: Xaa = any amino acid, where one of amino acids
      7 to 9 can be absent
<220> FEATURE:
<221> NAME/KEY: MISC_FEATURE
<222> LOCATION: (11)..(22)
<223> OTHER INFORMATION: Xaa = any amino acid, where up to 8 of the
      amino acids 11 to 22 can be absent
<220> FEATURE:
<221> NAME/KEY: MISC_FEATURE
<222> LOCATION: (24)..(26)
<223> OTHER INFORMATION: Xaa = any amino acid
<220> FEATURE:
<221> NAME/KEY: MISC_FEATURE
<222> LOCATION: (28)..(32)
<223> OTHER INFORMATION: Xaa = any amino acid

<400> SEQUENCE: 31

Xaa Xaa Xaa Xaa Xaa Cys Xaa Xaa Xaa Cys Xaa Xaa Xaa Xaa Xaa Xaa
1               5                   10                  15

Xaa Xaa Xaa Xaa Xaa Xaa His Xaa Xaa Xaa His Xaa Xaa Xaa Xaa Xaa
            20                  25                  30

<210> SEQ ID NO 32
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(26)
<223> OTHER INFORMATION: Xaa = any amino acid, where up to 17 amino
      acids 7 to 26 can be absent

<400> SEQUENCE: 32

Phe Gln Cys Glu Glu Cys Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa His Ile Arg Ser His Thr
            20                  25                  30

Gly

<210> SEQ ID NO 33
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(3)
<223> OTHER INFORMATION: Xaa = any amino acid
```

```
<220> FEATURE:
<221> NAME/KEY: MISC_FEATURE
<222> LOCATION: (5)..(24)
<223> OTHER INFORMATION: Xaa = any amino acid, where up to 16 amino
      acids 5 to 24 can be absent
<220> FEATURE:
<221> NAME/KEY: MISC_FEATURE
<222> LOCATION: (26)..(29)
<223> OTHER INFORMATION: Xaa = any amino acid

<400> SEQUENCE: 33

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa His Xaa Xaa Xaa Xaa Cys
            20                  25                  30

<210> SEQ ID NO 34
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (7)..(26)
<223> OTHER INFORMATION: Xaa = any amino acid, where up to 16 amino
      acids 7 to 26 can be absent

<400> SEQUENCE: 34

Val Lys Cys Phe Asn Cys Xaa Xaa Xaa Xaa Xaa Xaa Xaa Xaa Xaa
1               5                   10                  15

Xaa Xaa Xaa Xaa Xaa Xaa Xaa Xaa Xaa Xaa His Thr Ala Arg Asn Cys
            20                  25                  30

Arg

<210> SEQ ID NO 35
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (10)..(29)
<223> OTHER INFORMATION: Xaa = any amino acid, where up to 16 amino
      acids 10 to 29 can be absent

<400> SEQUENCE: 35

Met Asn Pro Asn Cys Ala Arg Cys Gly Xaa Xaa Xaa Xaa Xaa Xaa
1               5                   10                  15

Xaa Xaa Xaa Xaa Xaa Xaa Xaa Xaa Xaa Xaa Xaa Xaa Xaa His Lys Ala
            20                  25                  30

Cys Phe

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

His His His His His His
1               5
```

```
<210> SEQ ID NO 37
<211> LENGTH: 4
<212> TYPE: PRT
<213> ORGANISM: Artificial Sequence
<220> FEATURE:
<223> OTHER INFORMATION: Synthetic

<400> SEQUENCE: 37

Gly Gly Gly Gly
1

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Gly Gly Gly Gly Gly
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic

<400> SEQUENCE: 39

Gly Gly Gly Gly Gly Gly
1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic

<400> SEQUENCE: 40

Gly Gly Gly Gly Gly Gly Gly
1               5
```

CYTOMODULATING PEPTIDES FOR TREATING INTERSTITIAL CYSTITIS

1. CROSS REFERENCES TO RELATED APPLICATIONS

This application claims the benefit of U.S. Provisional Application No. 60/426,684, filed 15 Nov. 2002, and U.S. Provisional Application No. 60/470,839, filed 15 May 2003, each of which is incorporated herein by reference.

2. TECHNICAL FIELD

This invention relates generally to methods and compositions for the treatment of bladder disorders and in particular to therapies directed to treatment of interstitial cystitis and related conditions.

3. BACKGROUND

The bladder is a membranous muscular organ used for storage of urine, maintenance of urine composition, and elimination of urine at appropriate intervals. Its structure is composed of four basic layers, comprising an epithelium, lamina propria, muscularis propria (i.e., detrusor muscle), and perivesical soft tissue. The epithelium, which lines the bladder and is in contact with the urine, is referred to as the transitional epithelium or urothelium and functions to maintain a chemical gradient between the urine and blood. Lying underneath the epithelium is the lamina propria, a layer of connective tissue and blood vessels. A layer of thin and often discontinuous smooth muscle, the muscularis mucosae, lies within the lamina propria. This superficial layer of smooth muscle is distinctive from the muscularis propria or detrusor muscle, which is a deep muscle layer consisting of thick smooth muscle bundles that form the wall of the bladder. Perivesical soft tissue comprises the outer layer of the bladder and consists of fat, fibrous tissue and blood vessels. Dysfunctions of the bladder are common and can have debilitating effects on the affected individual.

Interstitial cystitis (IC) is a bladder disease of unknown etiology. Clinical symptoms include chronic urinary frequency, urgency, nocturia, and bladder/pelvic pain. Although originally thought to primarily affect middle-aged women, IC occurs in both sexes and in all ages.

The literature describes two types of IC based on cytoscopic examinations of the bladder. Non-ulcerative IC, the most common form, is characterized by presence of glomerulations (ie., pinpoint bleeding) upon hydrodistention of the bladder. Ulcerative IC is seen in about 10% of patients and is defined by the presence of Hunner's ulcers, which are star shaped mucosal ulcerations on the bladder wall. A significant number of IC patients, however, show no symptoms upon cytoscopic examination, and there is no reliable correlation between severity of cytoscopic findings and clinical symptoms.

Histopathological indications are a denuded epithelium, prominent leukocyte and plasma cell infiltration in the lamina propria, vascular congestion, and fibrosis of the detrusor layer (MacDermott, J. P. et al., *J. Urol.* 145: 274-278 (1991)). These features, however, appear to be restricted to a small subgroup of patients diagnosed with pyuria and small bladder capacity. Neutrophils are seen only in association with ulcerations (Lynes, W. L. et al., *Amer. J. Surg. Pathol.* 14: 969-976 (1990)). Macrophages are rarely present in the inflamed sites, and inflammatory infiltrates are infrequent in the detrusor layer. Chronic inflammation is absent in many patients who show clinical symptoms. Because of this varying, inconsistent histopathology, diagnosis of IC may use a constellation of indications.

Various theories exist on causes of IC, including compromised epithelial integrity, infection, neurogenic inflammation, mast cell activation, and autoimmunity. Several studies suggest increased permeability of the epithelium in IC patients (see, e.g., Lavelle, J. P. et al., *Am. J. Physiol. Renal. Physiol.* 278: F540-F553 (2000)). Affected bladders show qualitative changes in mucosal glycosaminoglycan, ultrastructural defects in urothelium, and increased transport of urea. Pain and urgency occur in a majority of patients with IC upon intravesical instillation with KCl solution, suggestive of compromised epithelial structure. Similarly, a urea solution instilled into the bladder and then later drained has lower urea concentrations in IC patients versus control groups, indicating increased mucosal permeability in affected subjects.

Although infection is also suspected as an etiological agent, PCR analyses of biopsy samples have proved negative for presence of pathogenic bacteria (Keay, S. et al., *J. Urol.* 159: 280-283 (1998)). In addition, analysis for bacteria, fungi, and viruses in IC afflicted bladders has not detected any differences from unaffected patients (Duncan, J. L. et al., *Urology* 49: 48-51 (1997)). At present, evidence for a pathogenic cause is lacking.

Several studies suggest a role in IC of neurogenic inflammation involving neuropeptide Substance P and its receptor, neurokinin-1 receptor (NK-1 receptor). Stimulation of sensory neurons results in release of Substance P, which is known to trigger release of inflammatory modulators and histamine by mast cells. In animal models of IC, Substance P level is elevated in the bladder and urine (Hammond, T. G. et al., *Ann J. Physiol. Renal Physiol* 278: F440-F451 (2000)), and biopsies show increased density of Substance P containing nerve fibers. Intravesical administration of Substance P causes bladder inflammation in mice while desensitization of sensory fibers decreases urinary bladder hyperflexia. NK-1 receptor antagonists abrogate or reduce Substance P mediated cystitis, and bladder inflammation is attenuated in NK-1 receptor knockout mice (Saban, R. et al., *Amer. J. Path.* 156: 775-780 (2000)). Further suggestion for involvement of the Substance P pathway is indicated by increased expression of NK-1 receptor seen in bladder biopsies of patients with IC (Marchand, J. E. et, al., *Br. J. Urol.* 81:224-228 (1998)).

The postulated role of Substance P implicates mast cells in the physiological processes leading to IC. IC bladders have increased numbers of mast cells in the detrusor and submucosal layers, and elevated numbers of mast cells are found near Substance P containing sensory nerves. Mastocytosis is present in 30-65% of IC patients while levels of histamine and tryptase are elevated. Interestingly, experimentally induced bladder inflammation is absent in mast cell deficient mice Kit(W)/Kit(W-v) (see Saban, R. et al., *Physiol. Genomics* 10: 35-43 (2001); Saban, R. et al., *Am. J. Physiol. Renal Physiol.* 282: F202-F210 (2002)). It is theorized that elevated number of mast cells in conjunction with sensory peptides lead to mast cell mediated immune reactions. The predominant presence of mast cells in the detrusor layer, however, does not explain the compromised state of epithelium in IC. Moreover, very few inflammatory cells are found in the detrusor layer.

An autoimmune cause is suspected in IC because of an epidemiological association between IC and autoimmune diseases, such as lupus erythematosus, allergic asthma, multiple sclerosis, inflammatory bowel disease, and Sjorgren's disease. These autoimmune diseases are overrepresented in IC afflicted patients. However, lymphocyte phenotypes (e.g., CD4/CD8 cell ratios) in the peripheral blood of IC subjects are normal, in contrast to findings for autoimmune diseases lupus erythematosus, primary biliary cirrhosis, or multiple sclerosis (MacDermoft, J. P. et al., *J. Urol.* 145: 274-278 (1991)). Histological studies of bladder biopsies show increased lymphocyte infiltrates, but are contradictory as to the type of lymphocytes present in the various structures of the bladder (MacDermoft et al., supra.; Hanno, P. et al., *J. Urol.* 143: 278-281 (1990)). Although early studies also indicated presence of circulating bladder specific antibodies, subsequent results have shown conflicting data, suggesting that these humoral indications may be an indirect consequence of tissue damage. Consequently, no clear link has been established between immune system dysregulation and IC.

The presence of lymphocyte infiltrates and increased number of mast cells suggests some role of inflammatory network in IC. Conditioned medium obtained from cultured, activated mast cells can induce in an urothelial cell line synthesis of cytokines TNF-α, IL-1 b, and IL-8, and adhesion molecule ICAM-1 (Batler, R. A. et al., *J. Urol.* 168: 819-825 (2002)). On the other hand, inflammatory mediators are not significantly elevated in the urine of patients diagnosed with IC. Urinary concentrations of cytokines IL4, IL-10, IL-12, TNF-α, hGM-CSF, IL-1b and IFN-γ; prostaglandins E2, D2, and F2a; and thromboxanes are no different from unaffected individuals (Felson, D. et al., *J. Urol.* 152: 355-361 (1994); Peters, K. M. *Adult Urology* 54: 450-453 (1999)). Some patients with active IC show elevated levels of cytokines IL-2, IL-6, and IL-8, but not of major inflammatory cytokines TNF-α or IFN-γ (Peters, K. M., supra). The predominance of mast cells in the detrusor layer, which lacks inflammatory infiltrates, and the general absence of macrophages complicate the link between the inflammatory cascade and IC. Interestingly, BCG (bacilli Calmette-Guerin), which shows some efficacy in ameliorating the symptoms of IC, is known to increase levels of IL-1, IL-2, IFN-γ and TNF-α in urine following intravesical instillation in the bladder (see Peters, K. M. et al., supra; Bohle, A. *J. Urol* 144: 5964 (1990)).

Treatments for IC are few and varied, particularly given the unknown etiology of the disease. BCG, as indicated above, has shown some efficacy in treating IC symptoms. Pentosan polysulfate sodium (Elmiron®), a heparin derivative, is believed to help repair and protect damaged bladder epithelium, but also inhibits release of histamine from mast cells (Chiang, G. et al., *J. Urol.* 164(6):2119-2125 (2000)). Dimethyl sulfoxide (DMSO) reduces bladder pain and is suggested to have an anti-inflammatory effect. Immunosuppressive agents cyclosporin (Forsell, T. et al., *J. Urol.* 155:1591-1593 (1996)) and methotrexate (Moran, P. A. et al., *Aust N Z J Obstet Gynaecol.* 39: 468-471 (1999)) provides variable effectiveness in ameliorating IC symptoms. Given the lack of standard, effective therapy for IC, there is a need in the art for other efficacious, therapeutic treatments. Accordingly, the present invention provides methods and compositions for the treatment of IC.

4. SUMMARY

The present invention relates to methods and compositions for treating disorders of the bladder, particularly for the treatment of interstitial cystitis (IC) and related conditions. The peptide compositions are known to have manifold biological activities, including modulating the immune response, modulating levels of inflammatory cytokine, and regulating signal transduction pathways mediated by p38 MAP kinase, JNK, TRAF, and IRAK. The diverse properties of the oligopeptide extend to affecting various manifestations of IC, including, inhibiting histamine release, altering levels of Substance P, modulating levels of nerve growth factor (NGF), and modulating levels of cytokines TNF-α, IFN-γ, IL-6 and IL-12. The compositions are also shown to reduce polymorphonuclear cell, T-cell, and mast cell infiltration into affected tissues, and maintain or restore the bladder urine/blood barrier.

Accordingly, methods are provided for treatment of IC, comprising administering to an affected subject a therapeutically effective amount of a composition comprising an RDP58 oligopeptide. Acute and/or chronic forms of IC may be treated by the compositions.

Given the manifold effects of the RDP58 oligopeptides, the methods provided herein also relate to modulating, preferably ameliorating, one or more manifestations associated with IC, many of which are believed to contribute to development of the condition. The general method comprises contacting tissues or cells affected by IC with a pharmaceutically effective amount of an RDP58 composition to ameliorate the disease manifestation.

In one aspect, mast cells are contacted with a pharmaceutically effective amount of an RDP58 composition to inhibit or reduce histamine levels in disease affected tissues or cells.

In another aspect, disease affected tissues or cells are contacted with a pharmaceutically effective amount of the oligopeptide to reduce Substance P levels.

In a further aspect, the disease affected tissues or cells are contacted with a pharmaceutically effective amount of the oligopeptide to reduce NGF levels.

Additionally, the disease affected tissues or cells are contacted with a pharmaceutically effective amount of the oligopeptide to modulate levels of cytokines TNF-α, IFN-γ, IL-6 and IL-12.

Integrity of the urine/blood barrier may also be maintained or restored by treatment with a pharmaceutically effective amount of the subject compositions. The oligopeptide limits degradation of bladder permeability and, in the chronic condition, restores bladder permeability characteristics to those of unaffected bladders.

Compositions of RDP58 include use of other agents effective for treating IC or associated conditions. Combination therapies include use of steroids, immunosuppressants, tricyclic antidepressants, sulfated polysaccharides, DMSO, capsaicin, antihistamines, or mixtures thereof.

Provided for the treatments are various pharmaceutical compositions comprising an RDP58 oligopeptide and a pharmaceutically acceptable carrier. The carrier includes excipients or diluents for administration to an affected subject, tissue or cells, particularly diluents for intravesical delivery.

Administration of the peptides may be by any convenient means, including by direct application or administration of the oligopeptide, or the nucleic acids encoding the desired peptide, to the afflicted tissue or cells. Preferred are intravesical instillations of the subject compositions. Alternatively, the peptides are administered indirectly via routes which result in delivery of the peptide to the bladder, including intravenous and parental administration.

5. BRIEF DESCRIPTION OF THE DRAWINGS

Figure 1:
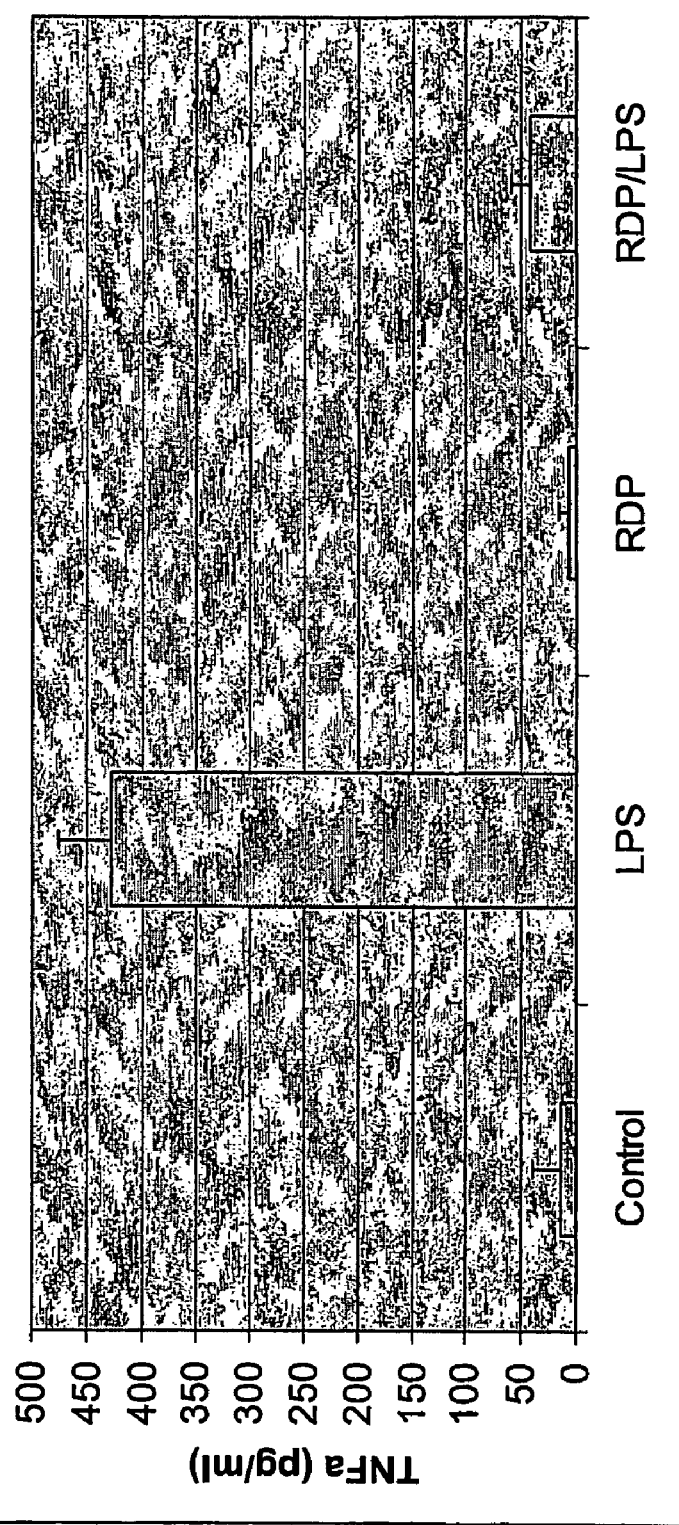
FIG. 1 shows the levels of TNF-α in bladder tissue after ex vivo treatment with lipopolysaccharide (LPS), RDP58 peptide (bc1nL), LPS+RDP58 peptide, or media alone (control).
Figure 2:
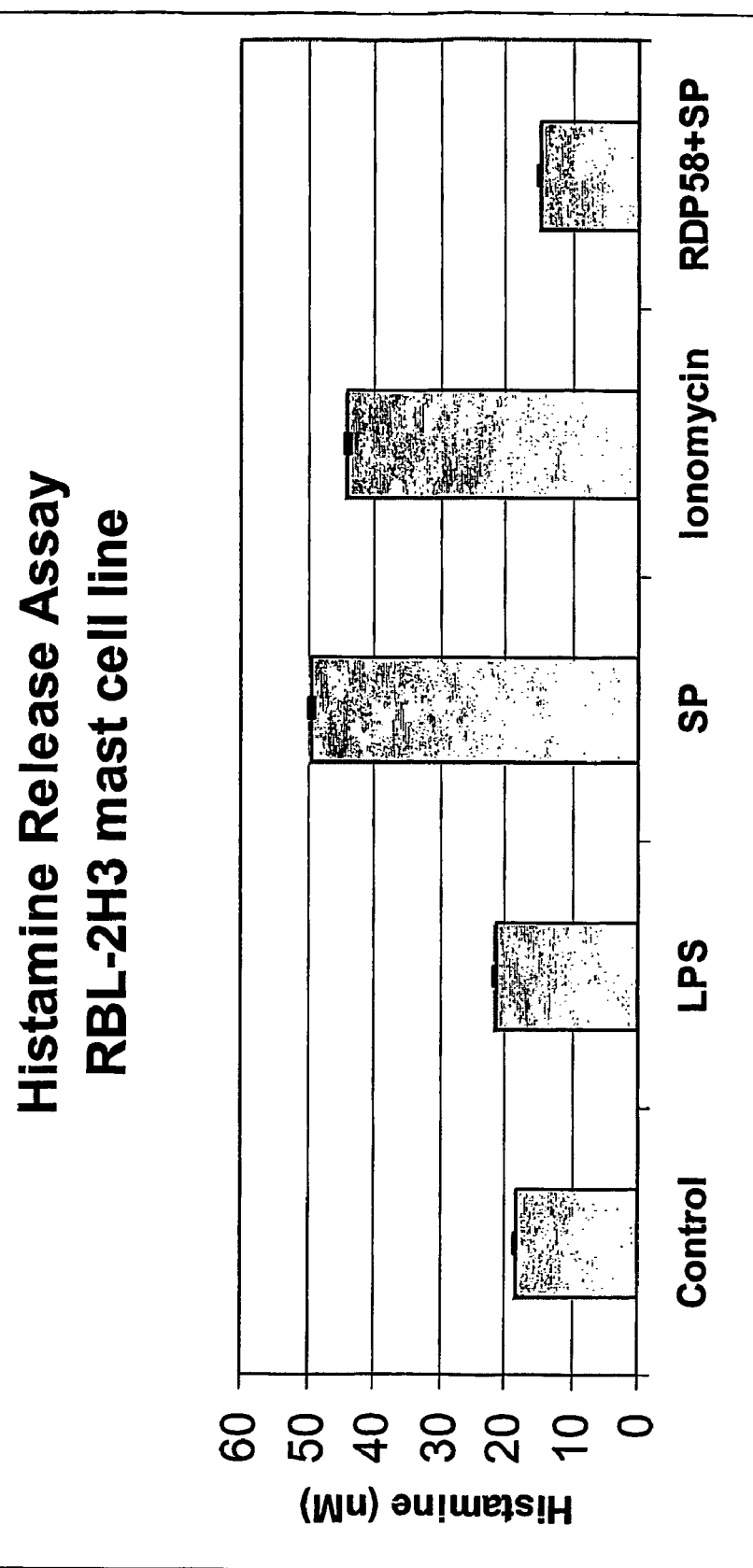
FIG. 2 shows histamine release from rat basophil leukemia cells (RBL-2H3) induced with LPS, Substance P (SP), or lonomycin, and the effect of RDP58 in inhibiting histamine release in culture.

FIGS. 3A-3D show effect of RDP58 oliogopeptide on levels of biochemical markers in an experimentally induced acute form of IC: FIG. 3A—TNF-α; FIG. 3B—IL-6; FIG. 3C—Substance P; FIG. 3D—Histamine release; and FIG. 3E—NGF.

FIG. 4 shows bladder permeability as determined by measuring serum levels of FITC-dextran following intravesicle instillation of FITC-dextran in experimentally induced model of acute IC.

FIGS. 5A and 5B show levels of FITC-dextran found in serum under various treatment conditions and the effect of RDP58 oligopeptide in maintaining integrity of the urine/blood barrier. Where indicated, acute cystitis is induced by instilling LPS into the animals (i.e., "LPS" and "RDP58"). Fluorescence of various dilutions of serum are shown in FIG. 5A.

FIG. 6 shows approximate percentages of FITC-dextran in serum following bladder instillation with LPS or LPS+RDP58. Percentages refer to the fraction of FITC-dextran found in the serum as compared to the amount instilled into the bladder.

FIGS. 7A and 7B show effect of RDP58 peptide on TNF-α and IL-6 expression in an animal model of chronic IC.

FIG. 8 shows effect of RDP58 on bladder permeability in an animal model of chronic IC.

FIGS. 9A-9D show hematoxylln-eosin stained and CD45 immunostained bladder tissue sections in an animal model of chronic IC. Animals were instilled with either saline (control) or LPS.

FIGS. 10A-10F show CD3 immunostained bladder tissue sections from animals subjected to instillation with only saline in an animal model of chronic IC.

FIGS. 11A-11H show CD3 immunostained bladder tissue sections in an animal model of chronic IC 72 hrs (FIGS. 11A-11D) or 7 days (FIGS. 11E-11F) after final LPS instillation. Tissue sections show increased presence of CD3 positive cells as compared to saline treated animals.

FIGS. 12A-12D show CD3 immunostained tissue sections in animals exposed to LPS and subsequently treated with RDP58 oligopeptide in an animal model of chronic IC (FIG. 12A: 24 hrs after RDP58 treatment; FIG. 12B: 72 hrs after RDP58 treatment.). RDP58 treatment results in reduction of CD3 positive cells.

6. DETAILED DESCRIPTION

6.1 Treatment of Interstitial Cystitis

The present invention relates to methods and compositions for the treatment of interstitial cystitis (IC) and related conditions. Compositions relate to compounds disclosed in PCT Publication WO 98/46633 and co-pending U.S. patent applications Ser. No. 09/028,083 and Ser. No. 08/838,916, all of which are expressly incorporated herein by reference. These oligopeptide compounds, described as modulating the immune response and inhibiting inflammatory cytokine production, have been further shown to affect cellular signalling pathways mediated by p38 MAP kinase, JNK, TRAF, and IRAK. Signalling through these pathways is associated with a diverse set of disease states. It is shown here that the manifold biological activities of the RDP58 peptides have the properties of modulating various manifestations of IC, thereby providing a therapeutic agent for treating the multifaceted condition.

"Interstitial cystitis" or "IC" as used herein refers to a disorder, disease, or condition characterized by one or more manifestations of interstitial cystitis. Manifestations included clinical symptoms (e.g., urinary frequency and urgency, nocturia, and bladder/pelvic pain); diagnostic indications (e.g., response to instillation of KCl solution, glomerulations on hydrodistension; presence of Hunner's ulcers), and histopathological indications, such as lymphocyte infiltration, elevated numbers of mast cells, and changes in epithelial structure (e.g., bladder permeability). Other manifestations are changes in expression or presence of disease markers, including, but not limited to, Substance P, IL-2, IL-6, IL-8, glycoprotein 51, antiproliferative factor, nerve growth factor (NGF); histamine, and others (see, e.g., Erickson, D. R., *Urology* 57 (Supplement 6A): 15-21 (2001), hereby incorporated by reference). Although one manifestation may be used as an indicator of IC, preferably more than one is used, and more preferably a combination of manifestations is used, including combinations of clinical symptoms, histological indications, and molecular/biochemical markers.

The peptide or oligopeptide compositions of the present invention are found to modulate, preferably ameliorate, various manifestations in animal models of IC, both acute and chronic. Amerlioration is an improvement from the diseased state as reflected in changes to various manifestations of the disease condition. It is shown here that the RDP58 peptides can alter levels of inflammatory cytokines, particularly expression of TNF-α and IFN-γ in affected bladders; reduce histamine release from mast cells; affect expression of Substance P peptide; and affect expression of nerve growth factor (NGF). At the histological level, treatment with RDP58 peptides attenuates infiltration by polymorphonuclear (PMN) cells, T cells, and mast cells; ameliorates the edema associated with IC; and reduces or limits degradation of the blood/urine barrier in the bladder.

Accordingly, the present invention provides for methods of treating IC by administering to an afflicted subject a therapeutically effective amount of a composition comprising an RDP58 oligopeptide. Treatment may be for acute IC or chronic IC. Acute IC is associated with mast cell, neutrophil, and macrophage infiltration while T cell infiltration is normally associated with the chronic condition. As disclosed herein, the RDP58 peptides are found to limit polymorphonuclear cell and mast cell infiltrations in acute cystitis models. For chronic cystitis, the subject peptides can reduce T-cell infiltration in affected tissues, as determined by presence of CD3 or CD45 positive cells. It is to be understood that these descriptions of acute and chronic conditions are not meant to be limiting as to the conditions treatable by the oligopeptides, but simply reflects the state of knowledge in the art in distinguishing disease states.

The peptides are also used to modulate, and preferably ameliorate, one or more manifestations associated with IC. The disease affected tissue or cells are contacted with a pharmaceutically effective amount of a composition comprising an RDP58 oligopeptide in an amount sufficient to modulate or ameliorate the manifestation of IC. Accordingly, in one aspect, the peptides are used to reduce or inhibit mast cell activation in IC, as indicated by release of histamine or other mast cell granule contents, such as proteoglycans and serine proteases. It is suggested that mast cell activation is followed by synthesis of chemokines, cytokines, and lipid mediators (e.g., prostaglandins and leukotrienes), which contribute to chronic inflammation by promoting release of additional cytokines and chemokines and recruitment of inflammatory cells, such as basophils, eisinophils, and macrophages. Mastocytosis is observed in IC, and the severity of experimentally induced cystitis is attenuated in mast cell deficient mouse (Bjorling, D. E., *J Urol.* 162(1):231-236 (1999)). As demonstrated herein, RDP58 peptides are capable of reducing levels of histamine release from mast cells and also reducing the numbers of mast cells present in IC affected tissues.

In another aspect, the RDP58 peptides are used to reduce Substance P levels in IC affected tissue or cells. Substance P is constitutively released from the bladder wall (Saban, R. et al., *Br. J. Urol.* 79:516-524 (1997)). Upon release from afferent nerve endings in bladders affected with IC, Substance P is believed to trigger mast cell activation and histamine release, thereby inducing or exacerbating the disease state. In turn, the products of mast cell degranulation can activate sensory C fibers to release Substance P, generating a positive feedback loop for continued activation of mast cells (Suzuki, R. et al., *J. Immunol.* 163:2410-2415 (1999)). Substance P is also a mediator in the nociceptive pathway through its binding and activation of neurokinin receptors and may contribute to the bladder/pelvic pain that is commonly associated with IC. Accordingly, in a further embodiment, reduction in Substance P levels obtained by use of the subject peptides may also be beneficial in reducing the pain associated with the disease.

The RDP58 peptides are also used to reduce levels or expression of nerve growth factor (NGF) in IC affected tissues or cells. NGF levels are increased in several bladder conditions, including idiopathic sensory urgency and IC (Lowe, E. M. et al., *Br. J. Urol.* 79(4):572-527 (1997)). Nerve growth factor may sensitize afferent nerves and induce bladder hyperactivity, which is one of the symptoms in the constellation of conditions that define IC. In addition, NGF may increase sensitivity of nociceptive pathways, thereby contributing to the pain in the disease condition (Lowe, supra). Similar to the effects of reducing levels of Substance P, reduction in NGF obtained by use of the subject peptides may also have the benefit of reducing pain.

In a further aspect, RDP58 peptides are used to reduce levels of or inhibit expression of various cytokines, particularly TNF-α, IFN-γ, IL-6, and IL-12, in IC affected tissues or cells. TNF-α, along with IFN-γ, is a key inflammatory cytokine, responsible for eliciting and propagating the inflammatory response. Production of these cytokines leads to activation of macrophages, which in turn produce additional pro-inflammatory cytokines, including IL-1; TNF-α; chemokines, including IL-8; and mediators IL-6, IL-12, and IL-18. These interrelated networks of cytokines, chemokines, and lipid mediators amplify the inflammatory cascade by further activation of T lymphocytes and macrophages, and recruitment of blood borne effector cells that results in secretion of more inflammatory mediators, which ultimately lead to tissue injury. IL-6 and IL-12 may contribute to the inflammatory response by eliciting a humoral response to tissue damage.

In yet a further aspect, RDP58 peptides are used to maintain or restore the urine/blood barrier in IC affected bladder. The epithelium of bladders with cystitis shows structural and molecular differences from unaffected subjects and may account for the compromised permeability characteristics of the epithelium, as evidenced by increased mucosal permeability in patients with IC to instilled urea or sugars (see, e.g., Erickson, D. R. et al., *J. Urol.* 164(2):419-422 (2000)). This disruption of the mucosal lining and corresponding compromise of the urine/blood barrier is further indicated by the presence of blood in the urine of IC patients. Treatment with RDP58 peptide is shown here to maintain or restore permeability characteristics of bladders in both acute and chronic models of IC.

Generally, the method of treating IC, and associated conditions, comprises administering to a patient or subject a pharmaceutically effective amount or a therapeutically effective amount of an RDP58 composition, or mixtures thereof.

By "treatment" herein is meant therapeutic or prophylactic treatment, or a suppressive measure for the disease, disorder or undesirable condition. Treatment encompasses administration of the subject peptides in an appropriate form prior to the onset of disease symptoms and/or after clinical manifestations, or other manifestations, of the disease to reduce disease severity, halt disease progression, or eliminate the disease. Prevention of the disease includes prolonging or delaying the onset of symptoms of the disorder or disease, preferably in a subject with increased susceptibility to the disease. Efficacy of treatment is measurable based on the manifestations described above.

For use as treatment or prophylaxis, the RDP 58 oligopeptides may be used alone or in combination with other therapeutic agents. In this context, the oligopeptides used are either a single oligopeptide sequence, or an admixture of different oligopeptide sequences of the present invention, or an admixture that includes natural analogs of the peptides of the present invention, as further described below.

Other therapeutic or pharmaceutically active agents used to treat the disease condition may be used as an adjunct to treatment with the RDP58 oligopeptides. With reference to IC, agents that may be useful in combination with the oligopeptides include, by way of example and not limitation, steroids (e.g., dexamethasone, etc.), immune suppressants (e.g., cyclosporin, methotrexate, etc.); tricyclic anti-depressants (e.g., amitriptyline, doxapin); sulfated polysaccharides (e.g., pentosan polysulfate sodium); antihistamines (e.g., hydroxyzine, cimetidine, etc.); DMSO; and capsaicin, a C-fiber afferent neurotoxin (Fagerli, J., *Can J Urol.* 6(2):737-744 (1999)).

In circumstances where the cystitis is attributed to a pathogen, the peptides of the present invention may be used with drugs directed against eliminating or killing the pathogen. These include antibiotics, anti-fungal agents, anti-protozoan agents, and anti-viral agents, as is well known in the art. These drugs may be used prior to, concomitantly with, or subsequent to treatment with the peptides described herein.

It is to be understood that although the discussions above relate to treatment of IC, the present methods and compositions are useful for treating non-interstitial cystitis characterized by one or more manifestations described above for IC. Non-interstitial cystitis include, as examples, radiation cystitis, bacterial cystitis, and chemical cystitis. As used herein, radiation cystitis refers to a cystitis arising from exposure of the bladder to cell damaging doses of radiation, such as Ionizing radiation (e.g., x-rays and γ-rays) used in external or intracavitary radiation therapy for primary urothelial neoplasms or other pelvic malignancies (e.g., prostate, bladder, colon/rectum). Bacterial cystitis refers to cystitis resulting from a bacterial infection of the bladder and/or urinary tract. Bacterial pathogens suspected as causative agents include, *E. coli., Staphylococcus saprophyticus, Proteus mirabilis, Kiebsiella* spp, or *Enterococci*. Chemical cystitis refers to cystitis arising from exposure of the bladder to toxic or irritating chemicals. Exemplary chemical cystitis is seen in bladder cancer patients undergoing chemotherapy by intravesical instillation or bladder implantation of chemotherapeutic drugs, such as triethylenethiophosphoramide, cyclophosphamide, mitomycin-C, adriamycin, and doxorubicin and its analog valrubicin.

6.2 Peptide/Oligopeptide Compositions

The RDP58 peptide compositions suitable for treating IC will comprise at least one peptide, polypeptide or oligopeptide described in PCT Publication WO 98/46633 and co-pending U.S. patent application Ser. Nos. 09/028,083 and 08/838,916, expressly incorporated herein by reference. The peptides are characterized therein as being capable of inhibiting the cytotoxic activity of lymphocytic cells, inhibiting the production of inflammatory cytokines and inflammatory responses associated with those cytokines, inhibiting the activity of heme-containing enzymes and delaying the onset of autoimmune disease in a mammal at risk of developing such a disease.

The core sequence of the RDP58 peptide comprises two basic amino acids separated by from three to four hydrophobic amino acids, particularly three hydrophobic amino acids, and particularly where the N-terminus is a basic amino acid. Preferably, the C-terminal amino acid is an aromatic amino acid, particularly tyrosine. Of particular interest is where at least one of the oligopeptide core terminal amino acids is an oligopeptide terminal amino acid, which may be in the monomeric or oligomeric form of the compound.

Preferably, the RDP58 peptides for use in the compositions and methods disclosed herein comprise oligopeptides having the sequence B-X-X-X-B-X-X-X-J-Tyr (set forth as SEQ ID NO: 1), where B is a basic amino acid, preferably Lys or Arg, particularly Arg on at least one position, preferably at both positions; J is Gly, B or an aliphatic hydrophobic amino acid of from 5 to 6 carbon atoms, particularly Gly or B; and X is an aliphatic or aromatic amino acid. In one embodiment, at least three X amino acid residues are the same non-polar aliphatic amino acid, preferably at least four are the same non-polar aliphatic amino acid, more preferably at least five are the same non-polar aliphatic amino acid, and most preferably, all are the same non-polar aliphatic amino acid. In a preferred embodiment, the non-polar aliphatic amino acids are of from 5 to 6 carbon atoms, particularly 6 carbon atoms, particularly the non-polar aliphatic amino acids Val, Ile, Leu, and nL. Thus, in some embodiments, X is any amino acid other than a charged aliphatic amino acid, and preferably any amino acid other than a polar aliphatic amino acid.

Of the six amino acids indicated by X in the B-X-X-X-B-X-X-X-J-Tyr peptide sequence (set forth as SEQ ID NO: 1), preferably at least 3 are aliphatic amino acids of from 5 to 6 carbon atoms, more preferably at least 4 are aliphatic amino acids of from 5 to 6 carbon atoms, most preferably at least 5 are aliphatic amino acids of 5-6 carbon atoms, more particularly 6 carbon atoms. In a preferred embodiment, the aliphatic amino acids are non-polar aliphatic amino acids of from 5 to 6 carbon atoms, particularly Val, Ile, Leu, and nL. The other amino acids may be other uncharged aliphatic amino acids, particularly non-polar aliphatic amino acids or aromatic amino acids.

Compositions of particular interest will include an RDP58 peptide having the sequence Arg-U-X-X-Arg-X-X-X-J-Tyr (set forth as SEQ ID NO:2), wherein all of the symbols have been defined previously except U, which comprises an uncharged aliphatic amino acid or aromatic amino acid, particularly a non-polar aliphatic amino acid or aromatic amino acid.

The amino acids of the oligopeptide may be L- or D-isomer forms such that the peptides may have one or more amino acids of the D-stereoisomer, up to all of the amino acids. Additionally, the peptides may comprise oligomers of the subject peptides, particularly dimers thereof, or comprise a cyclic peptide, that is a ring structure, as further described below.

For the purposes of this invention, the amino acids, in the L or D-isomer configuration, will be broken down into the following categories:

1. Aliphatic
  (a) non-polar aliphatic: Gly, Ala, Val, nL, Ile, Leu
  (b) polar aliphatic:
    (1) uncharged: Cys, Met, Ser, Thr, Asn, Gln
    (2) charged: Asp, Glu, Lys, Arg
2. Aromatic:
  Phe, His, Trp, Tyr wherein Pro may be included in the non-polar aliphatic amino acids, but will normally not be included. "nL" represents norleucine, where the non-polar aliphatic amino acids may be substituted with other isomers.

Exemplary RDP-58 peptides include the following:

| bc # (SEQ ID NO) | | | | | | | | | | |
|---|---|---|---|---|---|---|---|---|---|---|
| 1 (SEQ ID NO:3) | Arg | Leu | Leu | Leu | Arg | Leu | Leu | Leu | Gly | Tyr |
| 2 (SEQ ID NO:4) | Arg | Val | Leu | Leu | Arg | Leu | Leu | Leu | Gly | Tyr |
| 3 (SEQ ID NO:5) | Arg | Ile | Leu | Leu | Arg | Leu | Leu | Leu | Gly | Tyr |
| 4 (SEQ ID NO:6) | Arg | Leu | Val | Leu | Arg | Leu | Leu | Leu | Gly | Tyr |
| 5 (SEQ ID NO:7) | Arg | Leu | Ile | Leu | Arg | Leu | Leu | Leu | Gly | Tyr |
| 6 (SEQ ID NO:8) | Arg | Leu | Leu | Val | Arg | Leu | Leu | Leu | Gly | Tyr |
| 7 (SEQ ID NO:9) | Arg | Leu | Leu | Ile | Arg | Leu | Leu | Leu | Gly | Tyr |
| 8 (SEQ ID NO:10) | Arg | Leu | Leu | Leu | Arg | Val | Leu | Leu | Gly | Tyr |
| 9 (SEQ ID NO:11) | Arg | Leu | Leu | Leu | Arg | Ile | Leu | Leu | Gly | Tyr |
| 10 (SEQ ID NO:12) | Arg | Leu | Leu | Leu | Arg | Leu | Val | Leu | Gly | Tyr |
| 11 (SEQ ID NO:13) | Arg | Leu | Leu | Leu | Arg | Leu | Ile | Leu | Gly | Tyr |
| 12 (SEQ ID NO:14) | Arg | Leu | Leu | Leu | Arg | Leu | Leu | Val | Gly | Tyr |
| 13 (SEQ ID NO:15) | Arg | Leu | Leu | Leu | Arg | Leu | Leu | Ile | Gly | Tyr |
| 14 (SEQ ID NO:16) | Arg | Trp | Leu | Leu | Arg | Leu | Leu | Leu | Gly | Tyr |
| 15 (SEQ ID NO:17) | Arg | Leu | Trp | Leu | Arg | Leu | Leu | Leu | Gly | Tyr |
| 16 (SEQ ID NO:18) | Arg | Leu | Leu | Trp | Arg | Leu | Leu | Leu | Gly | Tyr |
| 17 (SEQ ID NO:19) | Arg | Leu | Leu | Leu | Arg | Trp | Leu | Leu | Gly | Tyr |
| 18 (SEQ ID NO:20) | Arg | Leu | Leu | Leu | Arg | Leu | Trp | Leu | Gly | Tyr |
| 19 (SEQ ID NO:21) | Arg | Leu | Leu | Leu | Arg | Leu | Leu | Trp | Gly | Tyr |
| 20 (SEQ ID NO:22) | Arg | Tyr | Leu | Leu | Arg | Leu | Leu | Leu | Gly | Tyr |
| 21 (SEQ ID NO:23) | Arg | Leu | Tyr | Leu | Arg | Leu | Leu | Leu | Gly | Tyr |
| 22 (SEQ ID NO:24) | Arg | Leu | Leu | Tyr | Arg | Leu | Leu | Leu | Gly | Tyr |
| 23 (SEQ ID NO:25) | Arg | Leu | Leu | Leu | Arg | Tyr | Leu | Leu | Gly | Tyr |
| 24 (SEQ ID NO:26) | Arg | Leu | Leu | Leu | Arg | Leu | Tyr | Leu | Gly | Tyr |
| 25 (SEQ ID NO:27) | Arg | Leu | Leu | Leu | Arg | Leu | Leu | Tyr | Gly | Tyr |
| 1nL (SEQ ID NO:28) | Arg | nL | nL | nL | Arg | nL | nL | nL | Gly | Tyr |

A preferred embodiment of the RDP58 peptide comprises the sequence Arg-nL-nL-nL-Arg-nL-nL-nL-Gly-Tyr (set forth as SEQ ID NO:28), where nL is norleucine and all amino acids other than glycine are the D-stereoisomer.

Other RDP58 peptides are described in PCT application serial number PCT/US98/07231, filed 10 Apr. 1998, U.S. patent application Ser. No. 08/838,916, filed 11 Apr. 1997, and U.S. patent application Ser. No. 09/028,083 filed 23 Feb. 1998, each being expressly incorporated herein in its entirety by reference. Generally, the term "RDP58 peptide" or "RDP58 oligopeptide" as used herein is meant to encompass all of the foregoing peptide compounds.

In further embodiments, other known peptides such as HLA peptides and TCR peptides may be alternatively or additionally used in the subject invention as components of the subject RDP58 compositions. These include HLA-B α1-domain, particularly the amino acids from 75 to 84 and variations of this sequence where not more than 2 amino acids are replaced (see, e.g., WO 95/13288; U.S. Pat. Nos. 5,723, 128; 5,753,625; 5,888,512; 6,162,434; and 6,436,903; all publications expressly incorporated herein by reference). Also included are sequences based on the human TCR-α transmembrane region consisting of that sequence and sequences having not more than 2 mutations from that sequence (see Australian Application Nos. PN 0589 and PN 0590, filed Jan. 16, 1995, expressly incorporated herein by reference). These sequences include 2 basic amino acids, where the 2 basic amino acids are separated by 4 aliphatic hydrophobic amino acids, although the application indicates that from 3 to 5 hydrophobic amino acids may be present. By mutation is intended each substitution of one amino acid for another or an insertion or deletion, each being counted as one mutation. Generally, the term "peptide" or "oligopeptide" as used herein is meant to encompass all of the foregoing peptide compounds, as well as analogs, derivatives, fusion proteins and the like.

The subject peptides may be modified in a variety of conventional ways well known to the skilled artisan. The terminal amino group and/or carboxyl group of the peptide may be modified by alkylation, amidation, or acylation to provide esters, amides or substituted amino groups, where the alkyl or acyl group may be of from about 1 to 30, usually 1 to 24, preferably either 1 to 3 or 8 to 24, particularly 12 to 18 carbon atoms. This is done using conventional chemical synthetic methods. The peptide or derivatives thereof may also be modified by acetylation or methylation to alter the chemical properties, for example lipophilicity. Methods for acylating, and specifically for acetylating the free amino group at the N-terminus are well known in the art. For the C-terminus, the carboxyl group may be modified by esterification with alcohols or amidated to form —$CONH_2$, CONHR, or CONR, wherein each R is a hybroxycarbyl (1-6 carbons). Methods of esterification and amidation are done using well-known techniques. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see T. E. Creighton, *Proteins: Structure and Molecular Properties*, W.H. Freeman & Co. San Francisco, Calif., 1983).

In another aspect, one or both, usually one terminus of the peptide, may be substituted with a lipophilic group, usually aliphatic or aralkyl, of from 8 to 36, usually 8 to 24 carbon atoms and fewer than two heteroatoms in the aliphatic chain, the heteroatoms usually being oxygen, nitrogen and sulfur. As further described below, the chain may be saturated or unsaturated, desirably having not more than 3 sites, usually not more than 2 sites of aliphatic unsaturation. Conveniently, commercially available aliphatic fatty acids, alcohols and amines may be used, such as caprylic acid, capric acid, lauric acid, myristic acid and myristyl alcohol, palmitic acid, palmitoleic acid, stearic acid and stearyl amine, oleic acid, linoleic acid, docosahexaenoic acid, etc. (see U.S. Pat. No. 6,225,444, hereby incorporated by reference). Preferred are unbranched, naturally occurring fatty acids between 14-22 carbon atoms in length. Other lipophilic molecules include glyceryl lipids and sterols, such as cholesterol. The lipophilic groups may be reacted with the appropriate functional group on the oligopeptide in accordance with conventional methods, frequently during the synthesis on a support, depending on the site of attachment of the oligopeptide to the support. Lipid attachment is useful where oligopeptides may be introduced into the lumen of the liposome, along with other therapeutic agents for administering the pepbdes and agents into a host. Increasing lipophilicity is also known to increase transport of compounds across endothelial cells and therefore useful in promoting uptake of such compounds from the intestine or blood stream into surrounding tissues.

In additional embodiments, either or both the N- and C-terminus of the peptide may be extended by not more than a total of about 100, usually not more than a total of about 30, more usually not more than about 20 amino acids, often not more than about 9 amino acids, where the amino acids will have fewer than 25%, more usually fewer than 20% polar amino acids, more particularly, fewer than 20% which are charged amino acids. Thus, extensions of the above sequences in either direction are mainly done with lipophilic, uncharged amino acids, particularly non-polar aliphatic amino acids and aromatic amino acids. The peptides may comprise L-amino acids, D-amino acids, or mixtures of D- and L-amino acids. Exceptions to the number of amino acid extensions are contemplated when the oligopeptides are expressed as fusion or chimeric proteins, as described below.

The peptides may also be in the form of oligomers, particularly dimers of the peptides, which may be head to head, tail to tail, or head to tail, there being not more than about 6 repeats of the peptide. The oligomer may contain one or more D-stereoisomer amino acids, up to all of the amino acids. The oligomers may or may not include linker sequences between the peptides. When linker sequences are used, suitable linkers include those comprising uncharged amino acids and (Gly)n (SEQ ID NOS:37-40), where n is 1-7, Gly-Ser (e.g., $(GS)_n$, $(GSGGS)_n$ (set forth as SEQ ID NO:29), and $(GGGS)_n$ (set forth as SEQ ID NO:30), where n is at least 1), Gly-Ala, Ala-Ser, or other flexible linkers, as known in the art. Linkers of Gly or Gly-Ser may be used since these amino acids are relatively unstructured, which allows interaction of individual peptides with cellular target molecules and limits structural perturbations between peptides of the oligomer. It is to be understood that linkers other than amino acids may be used to construct the oligomeric peptides.

Peptides may also be in a structurally constrained form, such as cyclic peptides of from about 9-50, usually 12 to 36 amino acids, where amino acids other than the specified amino acids may be present as a bridge. Thus, for example, addition of terminal cysteines allows formation of disulfide bridges to form a ring peptide. In some instances, one may use other than amino acids to cyclize the peptide. Bifunctional crosslinking agents are useful in linking two or more amino acids of the peptide. Other methods for ring formation are described in Chen, S. et al., *Proc. Natl. Acad. Sci. USA* 89:5872-5876 (1992); Wu, T. P. et al., *Protein Engineering* 6:471478 (1993); Anwer, M. K. et al., *Int. J. Pep. Protein Res.*

36:392-399 (1990); and Rivera-Baeza, C. et al. *Neuropeptides* 30: 327-333 (1996); all references incorporated by reference. Alternatively, structurally constrained peptides are made by addition of dimerization sequences to the N- and C-terminal ends of the peptide, where interaction between dimerization sequences lead to formation of a cyclic type structure (see, e.g., WO/0166565, incorporated by reference). In other instances, the subject peptides are expressed as fusions to other proteins, which provide a scaffold for constrained display on a surface exposed structure, such as a loop of a coiled-coil or β-turn structure.

Depending upon their intended use, particularly for administration to mammalian hosts, the subject peptides may also be modified by attachment to other compounds for the purposes of incorporation into carrier molecules, changing peptide bioavailability, extend or shorten half-life, control distribution to various tissues or the blood stream, diminish or enhance binding to blood components, and the like. The subject peptides may be bound to these other components by linkers which are cleavable or non-cleavable in the physiological environment such as blood, cerebrospinal fluid, digestive fluids, etc. The peptides may be joined at any point of the peptide where a functional group is present, such as hydroxyl, thiol, carboxyl, amino, or the like. Desirably, modification will be at either the N-terminus or the C-terminus. For instance, the subject peptides may be modified by covalently attaching polymers, such as polyethylene glycol, polypropylene glycol, carboxymnethyl cellulose, dextran, polyvinyl alcohol, polyvinylpyrrolidine, polyproline, poly(divinyl-ether-co-maleic anhydride), poly(styrene-c-maleic anhydride), etc. Water-soluble polymers, such a polyethylene glycol and polyvinylpyrrolidine are known to decrease clearance of attached compounds from the blood stream as compared to unmodified compounds. The modifications can also increase solubility in aqueous media and reduce aggregation of the peptides.

6.3 Peptide Conjugates and Fusion Proteins

In another aspect, the peptide is preferably conjugated to small molecules for detection and isolation of the peptides, and to target or transport the oligopeptide into specific cells, tissues, and organs. Small molecule conjugates include haptens, which are substances that do not initiate an immune response when introduced by themselves into an animal. Generally, haptens are small molecules of molecular weight less than about 2 kD, and more preferably less that about 1 kD. Haptens include small organic molecules (e.g., p-nitrophenol, digoxin, heroin, cocaine, morphine, mescaline, lysergic acid, tetrahydrocannabinol, cannabinol, steroids, pentamidine, biotin, etc.). Binding to the hapten, for example for purposes of detection or purification, are done with hapten specific antibodies or specific binding partners, such as avidin which binds biotin.

Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the oligopeptide to form a β-O linked glycoside, enhances transport of the glycoside derivative via glucose transporters (Polt, R. et al., *Proc. Natl. Acad. Sci. USA* 91: 7144-7118 (1994); Oh et al., *Drug Transport and targeting*, in Membrane Transporters as Drug Targets, 59-88 (Amidon, G. L. and Sadee, W. eds.), Plenum Press, New York, (1999). Both of these types of modifications are encompassed within the scope of the present invention.

The oligopeptides may have attached various label moieties such as radioactive labels and fluorescent labels for detection and tracing. Fluorescent labels include, but are not limited to, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BIODIPY, $Cy^5$, etc.

In one aspect, the peptides are joined to a wide variety of other peptides or proteins for a variety of purposes. The peptides may be linked to peptides or proteins to provide convenient functionalities for bonding, such as amino groups for amide or substituted amine formation, e.g., reductive amination; thiol groups for thioether or disulfide formation; carboxyl groups for amide formation; and the like. Of particular interest are peptides of at least 2, more usually 3, and not more than about 60 lysine groups, particularly polylysines of from about 4 to 20, usually 6 to 18 lysine units, referred to as multiple antigenic peptide system (MAPS), where the subject peptides are bonded to the lysine amino groups, generally at least about 20%, more usually at least about 50%, of available amino groups, to provide a multipeptide product (Butz, S. et al., *Pept. Res.* 7: 20-23 (1994)). In this way, molecules having a plurality of the subject peptides are obtained where the orientation of the subject peptides is in the same direction; in effect, this linking group provides for tail-to-tail di- or oligomerization.

In another aspect, other naturally occurring or synthetic peptides and proteins may be used to provide a carrier immunogen for generating antibodies to the subject peptides, where the antibodies serve as reagents for detecting the oligopeptides or for identifying other peptides having a comparable conformation. Suitable carriers for generating antibodies include, among others, hemocyanins (e.g., Keyhole Limpet hemocyanin—KLH); albumins (e.g., bovine serum albumin, ovalbumin, human serum albumin, etc.); immunoglobulins; thyroglobulins (e.g., bovine thyroglobulin); toxins (e.g., diptheria toxoid, tetanus toxoid); and polypeptides such as polylysine or polyalaninelysine. Although proteins are preferred carriers, other carriers, preferably high molecular weight compounds, may be used, including carbohydrates, polysaccharides, lipopolysaccharides, nucleic acids, and the like of sufficient size and immunogenicity. In addition, the resulting antibodies may be used to prepare anti-idiotypic antibodies which may compete with the subject peptides for binding to a target site. These anti-idiotypic antibodies are useful for identifying proteins to which the subject peptides bind.

In another aspect, the peptides are conjugated to other peptides or proteins for targeting the oligopeptide to cells and tissues, or adding additional functionalities to the peptides. For targeting, the protein or peptide used for conjugation will be selected based on the cell or tissue being targeted for therapy (Lee, R. et al., *Arthritis. Rheum.* 46: 2109-2120 (2002); Pasqualini, R., *Q. J. Nucl. Med.* 43: 159-62 (1999); Pasgualinl, R., *Nature* 380: 364-366 (1996); hereby incorporated by reference). The proteins may also compromise polyamino acids including, but not limited to, polyarginine; and polylysine, polyaspartic acid, etc., which may be incorporated into other polymers, such as polyethylene glycol, for preparation of vesicles or particles containing the conjugated peptides.

In another aspect, the subject peptides may be expressed in conjunction with other peptides or proteins, to be a portion of the polypeptide chain, either internal, or at the N- or C-terminus to form chimeric proteins or fusion proteins. By "fusion polypeptide" or "fusion protein" or "chimeric protein" herein is meant a protein composed of a plurality of protein components that, while typically joined in the native state, are joined by the respective amino and carboxy termini through a peptide linkage to form a continuous polypeptide. Plurality in this context means at least two, and preferred embodiments generally utilize three to twelve components, although more may be used. It will be appreciated that the protein components can be joined directly or joined through a peptide linker/spacer as outlined below.

Fusion polypeptides may be made to a variety of peptides or proteins to display the subject oligopeptides in a conformationally restricted form, for targeting to cells and tissues, for targeting to intracellular compartments, tracking the fusion protein in a cell or an organism, and screening for other molecules that bind the oligopeptides. Proteins useful for generating fusion proteins include various reporter proteins, structural proteins, cell surface receptors, receptor ligands, toxins, and enzymes. Exemplary proteins include fluorescent proteins (e.g., *Aequodia victoria* GFP, *Renilla reniformis* GFP, *Renilla muelleri* GFP, luciferases, etc., and variants thereof); β-galactosidase; alkaline phosphatase; *E. coli*. maltose binding protein; coat proteins of filamentous bacteriophage (e.g., minor coat protein, pIII, or the major coat protein, pVIII, for purposes of phage display); T cell receptor; charybdotoxin; and the like.

Fusion proteins also encompass fusions with fragments of proteins or other peptides, either alone or as part of a larger protein sequence. Thus, the fusion polypeptides may comprise fusion partners. By "fusion partners" herein is meant a sequence that is associated with the peptide that confers all members of the proteins in that class a common function or ability. Fusion partners can be heterologous (i.e., not native to the host cell) or synthetic (ie., not native to any cell). The fusion partners include, but are not limited to, a) presentation structures, which provide the oligopeptides in a conformationally restricted or stable form; b) targeting sequences, which allow localization of the peptide to a subcellular or extracellular compartment; c) stability sequences, which affects stability or protection from degradation to the peptide or the nucleic acid encoding it; d) linker sequences, which conformationally decouples the oligopeptide from the fusion partner; and e) any combination of the above.

In one aspect, the fusion partner is a presentation structure. By "presentation structure" as used herein is meant a sequence that when fused to the subject peptides presents the peptides in a conformationally restricted form. Preferred presentation structures enhance binding interactions with other binding partners by presenting a peptide on a solvent exposed exterior surface, such as a loop. Generally, such presentation structures comprise a first portion joined to the N-terminus of the oligopeptide and a second portion joined to the C-terminal end of the oligopeptide. That is, the peptide of the present invention is inserted into the presentation structures. Preferably, the presentation structures are selected or designed to have minimal biological activity when expressed in the target cells.

Preferably, the presentation structures maximize accessibility to the peptides by displaying or presenting the peptide or an exterior loop. Suitable presentation structures include, but are not limited to, coiled coil stem structures, minibody structures, loops on β-turns, dimerization sequences, cysteine linked structures, transglutaminase linked structures, cyclic peptides, helical barrels, leucine zipper motifs, etc.

In one embodiment, the presentation structure is a coiled-coil structure, which allows presentation of the subject peptide on an exterior loop (Myszka, D. G. et al., *Biochemistry* 33: 2363-2373 (1994)), such as a coiled-coil leucine zipper domain (Martin, F. et al., *EMBO J.* 13: 5303-5309 (1994)). The presentation structure may also comprise minibody structures, which is essentially comprised of a minimal antibody complementary region. The minibody structure generally provides two peptide regions that are presented along a single face of the tertiary structure in the folded protein (Bianchi, E. et al., *J. Mol. Biol.* 236: 649-659 (1994); Tramontano, A. et al., *J. Mol. Recognit.* 7: 9-24 (1994)).

In another aspect, the presentation structure comprises two dimerization sequences. The dimerization sequences, which can be same or different, associate non-covalently with sufficient affinity under physiological conditions to structurally constrain the displayed peptide. Thus, if a dimerization sequence is used at each terminus of the subject oligopeptide, the resulting structure can display the subject peptide in a structurally limited or constrained form. A variety of sequences are suitable as dimerization sequences (see for example, WO 99/51625; incorporated by reference). Any number of protein-protein interaction sequences known in the art are useful for present purposes.

In a further aspect, the presentation sequence confers the ability to bind metal ions to generate a conformationally restricted secondary structure. Thus, for example, C2H2 zinc finger sequences are used. C2H2 sequences have two cysteines and two histidines placed such that a zinc ion is chelated. Zinc finger domains are known to occur independently in multiple zinc-finger peptides to form structurally independent, flexibly linked domains (Nakaseko, Y. et al., *J. Mol. Biol.* 228: 619-636 (1992)). A general consensus sequence is (5 amino acids)-C-(2 to 3 amino acids)-C-(4 to 12 amino acids)-H-(3 amino acids)-H-(5 amino acids) (set forth as SEQ ID NO:31). A preferred example would be -FQCEEC-random peptide of 3 to 20 amino acids-HIRSHTG (set forth as SEQ ID NO:32). Similarly, CCHC boxes having a consensus sequence -C-(2 amino acids)-C-(4 to 20 random peptide)-H-(4 amino acids)-C- set forth as SEQ ID NO:33) can be used, (Bavoso, A. et al., *Biochem. Biophys. Res. Commun.* 242: 385-389 (1998)). Other examples include (1) -VKCFNC-4 to 20 random amino acids-HTARNCR- (set forth as SEQ ID NO:34 ), based on the nucleocapsid protein P2; (2) a sequence modified from that of the naturally occurring zinc-binding peptide of the Lasp-1 LIM domain (Hammarstrom, A. et al., *Biochemistry* 35: 12723-32 (1996)); and (3) -MNPNCARCG-4 to 20 random amino acids-HIKACF- (set forth as SEQ ID NO:35), based on the NIVIR structural ensemble 1ZFP (Hammarstrom et al., supra).

In yet another aspect, the presentation structure is a sequence that comprises two or more cysteine residues, such that a disulfide bond may be formed, resulting in a conformationally constrained structure. That is, use of cysteine containing peptide sequences at each terminus of the subject oligopeptides results in cyclic peptide structures, as described above. A cyclic structure reduces susceptibility of the presented peptide to proteolysis and increases accessibility to its target molecules. As will be appreciated by those skilled in the art, this particular embodiment is particularly suited when secretory targeting sequences are used to direct the peptide to the extracellular space. In addition, sequences that are recognized and cleaved by proteases, such as the matrix metalloproteases (e.g., MMP-2 or gelatinase A, MMP-9 or gelatinase B, or MMP-7 or matrilysin), may be used. These residues are used to form circular peptides to increase peptide half-life or membrane permeability. Subsequent cleavage of the circular peptide with the appropriate protease releases the active, linear form of the peptide at the desired location.

In another embodiment, the fusion partner is a targeting sequence. Targeting sequences comprise binding sequences capable of causing binding of the expressed product to a predetermined molecule or class of molecules while retaining bioactivity of the expression product; sequences signalling selective degradation of the fusion protein or binding partners; and sequences capable of constitutively localizing peptides to a predetermined cellular locale. Typical cellular locations include subcellular locations (e.g., Golgi, endoplasmic recticulum, nucleus, nucleoli, nuclear membrane, mitochondria, secretory vesicles, lysosomes) and extracellular locations by use of secretory signals.

Various targeting sequences are known in the art. Targeting to nucleus is achieved by use of nuclear localization signals (NLS). NLSs are generally short, positively charged domains that directs the proteins in which the NLSs is present to the cells nucleus. Typical NLSs sequences include the single basic NLSs of SV40 large T antigen (Kalderon, D. et al., *Cell* 39: 499-509 (1984)); human retinoic acid receptor-s nuclear localization signal (NF-kB p50 and p65 (Ghosh, S. et al., *Cell* 62: 1019-1029 (1990)); Nolan, G. et al., *Cell* 64: 961-999 (1991)); and the double basic NLSs' as exemplified by nucleoplasmin (Dingwall, C. et al., *J. Cell Biol.* 107: 841-849 (1988)).

In another aspect, the targeting sequences are membrane-anchoring sequences. Peptides are directed to the membrane via signal sequences and stably incorporated in the membrane through a hydrophobic transmembrane domain (designated as TM). The TM segment is positioned appropriately on the expressed fusion protein to display the subject peptide either intracellularly or extracellularly, as is known in the art. Membrane anchoring sequences and signal sequences include, but are not limited to, those derived from (a) class I integral membrane proteins such as IL-2 receptor β-chain; Hatakeyama, M. et al., *Science* 244: 551-556 (1989)) and insulin receptor β-chain (Hetakeyama et al, supra); (b) class II integral membrane proteins such as neutral endopeptidase (Malfroy, B. et al *Biochem. Biophys. Res. Commun.* 144: 59-66 (1987)); and (c) type III proteins such as human cytochrome P450 NF25 (Hetakeyama et al, supra); and those from CD8,$_1$ ICAM-2, IL-8R, and LFA-1.

Membrane anchoring sequences also include the GPI anchor, which results in covalent bond formation between the GPI anchor sequence and the lipid bilayer via a glycosyl-phosphatidylinositol. GPI anchor sequences are found in various proteins, including Thy-1 and DAF (Homans, S. W. et al., *Nature* 333: 269-272 (1988)). Similarly, acylation sequences allow for attachment of lipid moieties, e.g., isoprenylation (ie., farnesyl and geranyl-geranyl; see Farnsworth, C. C. et al., *Proc. Natl. Aced. Sci. USA* 91: 11963-11967 (1994) and Aronheim, A. et al., *Cell* 78: 949-61 (1994)), myristoylation (Stickney, J. T. *Methods Enzymol.* 332: 64-77 (2001)), or palmitoylation. In one aspect, the subject peptide will be bound to a lipid group at a terminus, so as to be able to be bound to a lipid membrane, such as a liposome.

Other intracellular targeting sequences are lysozomal targeting sequences (e.g., sequences in LAMP-1 and LAMP-2; Uthayakumar, S. et al., *Cell Mol. Biol. Res.* 41: 405-420 (1995) and Konecki, D. S. et al., *Biochem. Biophys. Res. Comm.* 205:1-5 (1994)); mitochondrial localization sequences (e.g., mitochondrial matrix sequences, mitochondrial inner membrane sequences, mitochondrial intermembrane sequences, or mitochondrial outer membrane sequences; Shatz, G., *Eur. J. Biochem.* 165: 1-6 (1987)); endoplasmic recticulum localization sequences (e.g., calreticulin, Pelham, H. R. *Royal Soc. London Transactions* B: 1-10 (1992); adenovirus E3/19K protein, Jackson, M. R. et al., *EMBO J.* 9: 3153-3162 (1990)); and peroxisome localization sequences (e.g., luciferase peroxisome matrix sequence, Keller, G. A. et al., *Proc. Natl. Acad. Sci. USA* 4: 3264-3268 (1987)).

In another aspect, the targeting sequence is a secretory signal sequence which effects secretion of the peptide. A large number of secretory sequences are known to direct secretion of a peptide into the extracellular space when placed at the amino end relative to the peptide of interest, particularly for secretion of a peptide by cells, including transplanted cells. Suitable secretory signals included those found in IL-2 (Villinger, F. et al., *J. Immuno.* 155: 3946-3954 (1995)), growth hormone (Roskam, W. G. et al., *Nucleic Acids Res.* 7: 305-320 (1979)), preproinsulin, and influenza HA protein.

The fusion partner may further comprise a stability sequence, which confers stability to the fusion protein or the nucleic acid encoding it. Thus, for example, incorporation of glycines after the initiating methionine (e.g., MG or MGG) can stabilize or protect the fused peptide from degradation via ubiquitination as per the N-End rule of Varshavsky, thus conferring increased half-life in a cell.

Additional amino acids may be added for tagging the peptide for purposes of detection or purification. These sequences may comprise epitopes recognized by antibodies or sequences that bind ligands, such as metal ions. Various tag sequences and ligand binding sequences are well known in the art. These include, but is not limited to, poly-histidine (e.g., 6xHis tags (SEQ. ID NO: 36) , which are recognized by antibodies but also bind divalent metal ions); poly-histidine-glycine (poly-his-gly) tags; flu HA tag polypeptide; c-myc tag; Flag peptide (Hopp et al., *BioTechnology* 6: 1204-1210 (1988)); KT3 epitope peptide; tubulin epitope peptide (Skinner et al., *J. Biol. Chem.* 266: 15163-12166 (1991)); and T7 gene 10 protein peptide tag (Lutz-Freyermuth et al., *Proc. Natl. Acad. Sci.* USA 87: 6363-6397 (1990)).

Fusion partners include linker or tethering sequences for linking the peptides and for presenting the peptides in an unhindered structure. As discussed above, useful linkers include glycine polymers $(G)_n$ where n is 1 to about 7 (SEQ. ID. NOS: 37-40), glycine-serine polymers (e.g. $(GS)_n$, $(GSGGS)_n$ (SEQ ID NO: 29) and $(GGGS)_n$, where n is at least 1 (SEQ ID NO: 30)), glycine-alanine polymers, alanine-senne polymers, and other flexible linkers known in the art. Preferably, the linkers are glycine or glycine-serine polymers since these amino acids are relatively unstructured, hydrophilic, and are effective for joining the segments of proteins and peptides.

In the present invention, combinations of fusion partners may be used. Any number of combinations of presentation structures, targeting sequences, rescue sequences, tag sequences and stability sequences may be used with or without linker sequences.

6.4 Peptide Preparation and Salts

The RDP58 oligopeptides may be prepared in a number of ways. Chemical synthesis of peptides is well known in the art. Solid phase synthesis is commonly used and various commercial synthetic apparatuses are available, for example automated synthesizers by Applied Biosystems Inc., Foster City, Calif.; Beckman; etc. Solution phase synthetic methods may also be used, particularly for large-scale productions. By using these standard techniques, naturally occurring amino acids may be substituted with unnatural amino acids, particularly D-stereoisomers, and with amino acids with side chains having different lengths or functionalities. Functional groups for conjugating to small molecules, label moieties, peptides, or proteins, or for purposes of forming cyclized peptides may be introduced into the molecule during chemical synthesis. In addition, small molecules and label moieties may be attached during the synthetic process. Preferably, introduction of the functional groups and conjugation to other molecules minimally affects the structure and function of the subject peptide.

The peptides of the present invention may also be present in the form of a salt, generally in a salt form which is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

Synthesis of the oligopeptides and derivatives thereof may also be carried out by using recombinant techniques. For recombinant production, a nucleic acid sequence may be made which encodes a single oligopeptide or preferably a plurality of the subject peptides in tandem with an intervening amino acid or sequence, which allows for cleavage to the single peptide or head to tail dimers. Where methionine or tryptophane is absent, an intervening methionine or tryptophane may be incorporated, which allows for single amino acid cleavage using CNBr or BNPS-Skatole (2-(2-nitrophenylsulfenyl)-3-methyl-3-bromoindolenine), respectively. Alternatively, cleavage is accomplished by use of sequences that are recognized by particular proteases for enzymatic cleavage or sequences that act as self-cleaving sites (e.g., 2A sequences of apthoviruses and cardioviruses; Donnelly, M. L., *J. Gen. Virol.* 78:13-21 (1997); Donnelly, M. L., *J. Gen. Virol.* 82:1027-41 (2001), hereby incorporated by reference). The subject peptide may also be made as part of a larger peptide, which can be isolated and the oligopeptide obtained by proteolytic cleavage or chemical cleavage. The particular sequence and the manner of preparation will be determined by convenience, economics, purity required, and the like. To prepare these compositions, a gene encoding a particular peptide, protein, or fusion protein is joined to a DNA sequence encoding the oligopeptides of the present invention to form a fusion nucleic acid, which is introduced into an expression vector. Expression of the fusion nucleic acid is under the control of a suitable promoter and other control sequences, as defined below, for expression in a particular host cell or organism (Sambrook et al., Molecular Biology: A Laboratory Manual, Cold Spring Harbor Press, Cold Spring Harbor, N.Y. (3rd ed. 2001); Ausubel, F. et al., Current Protocols in Molecular Biology, John Wiley & Sons, New York, N.Y., (updates up to 2002) (1988); incorporated by reference).

For conjugating various molecules to the peptides of the present invention, functional groups on the oligopeptides and the other molecule are reacted in presence of an appropriate conjugating (e.g., crosslinking) agent. The type of conjugating or crosslinking agent used will depend on the functional groups, such as primary amines, sulfhydryls, carbonyls, carbohydrates and carboxylic acids being used. Agents may be fixatives and crosslinking agents, which may be homobifunctional, heterobifunctional, or trifunctional crosslinking agents (Pierce Endogen, Chicago, Ill.). Commonly used fixatives and crosslinking agents include formaldehyde, glutaraldehyde, 1,1-bis(diazoacetyl)-2-phenylethane, N-hydroxysuccinimide esters, dissuccimidyl esters, maleimides (e.g., bis-N-maleimido-1-8-octane), and carbodiimides (e.g., N-ethyl-N'-(3-dimethylaminopropyl)-carbodiimide; dicyclohexylcarbodiimide. Spacer molecules comprising alkyl or substituted alkyl chains with lengths of 2-20 carbons may be used to separate conjugates. Preferably, reactive functional groups on the oligopeptide not selected for modification are protected prior to coupling of the peptide to other reactive molecules to limit undesired side reactions. By "protecting group" as used herein is a molecule bound to a specific functional group which is selectively removable to reexpose the functional group (Greene, T. W. and Wuts, P. G. M. *Protective Groups in Organic Synthesis*, John Wiley & Sons, Inc., New York ($3^{ed}$. 1999)). The peptides may be synthesized with protected amino acid precursors or reacted with protecting groups following synthesis but before reacting with crosslinking agent. Conjugations may also be indirect, for example by attaching a biotin moiety, which can be contacted with a compound or molecule which is coupled to streptavidin or avidin.

For oligopeptides that have reduced activity in the conjugated form, the linkage between the oligopeptides and the conjugated compound is chosen to be sufficiently labile to result in cleavage under desired conditions, for example after transport to desired cells or tissues. Biologically labile covalent bonds, e.g., Imimo bonds and esters, are well known in the art (see, e.g., U.S. Pat. No. 5,108,921, hereby incorporated by reference). These modifications permit administration of the oligopeptides in potentially a less active form, which is then activated by cleavage of the labile bond.

6.5 Nucleic Acids, Expression Vectors, and Methods of Introduction

When synthesis or delivery of the oligopeptides are via nucleic acids encoding the subject peptides, the nucleic acids are cloned into expression vectors and introduced into cells or a host. The expression vectors are either self-replicating extrachromosomal vectors or vectors that integrate into the host chromosome, for example vectors based on retroviruses, vectors with site specific recombination sequences, or by homologous recombination. Generally, these vectors include control sequences operably linked to the nucleic acids encoding the oligopeptides. By "control sequences" is meant nucleic acid sequences necessary for expression of the subject peptides in a particular host organism. Thus, control sequences include sequences required for transcription and translation of the nucleic acids, including, but not limited to, promoter sequences, enhancer or transcriptional activator sequences, ribosomal binding sites, transcriptional start and stop sequences; polyadenylation signals; etc.

A variety of promoters are useful in expressing the peptides of the present invention. The promoters may be constitutive, inducible, and/or cell specific, and may comprise natural promoters, synthetic promoters (e.g., tTA tetracycline inducible promoters), or hybrids of various promoters. Promoters are chosen based on, among others, the cell or organism in which the proteins are to be expressed, the level of desired expression, and regulation of expression. Suitable promoters are bacterial promoters (e.g., pL1 phage promoter, tac promoter, lac promoter, etc.); yeast based promoters (e.g., GAL4 promoter, alcohol dehydrogenase promoter, tryptophane synthase promoter, copper inducible CUPI promoter, etc.), plant promoters (e.g., CaMV S35, nopoline synthase promoter, tobacco mosaic virus promoter, etc), insect promoters (e.g., Autographa nuclear polyhedrosis virus, Aedes DNV viral p& and p61, hsp70, etc.), and promoters for expression mammalian cells (e.g., ubiquitin gene promoter, ribosomal gene promoter, β-globin promoter, thymidine kinase promoter, heat shock protein promoters, and ribosomal gene promoters, etc.), and particularly viral promoters, such as cytomegalovirus (CMV) promoter, simian virus (SV40) promoter, and retroviral promoters.

By "operably linked" herein is meant that a nucleic acid is placed into a functional relationship with another nucleic acid. In the present context, operably linked means that the control sequences are positioned relative to the nucleic acid sequence encoding the subject peptides in such a manner that expression of the encoded peptide occurs. The vectors may comprise plasmids or comprise viral vectors, for example retroviral vectors, which are useful delivery systems if the cells are dividing cells, or lentiviral and adenoviral vectors if the cells are non-dividing cells. Particularly preferred are self-inactivating retroviral vectors (SIN vectors), which have inactivated viral promoters at the 3'-LTR, thereby permiting control of expression of heterologous genes by use of non-viral promoters inserted into the viral vector (see, e.g., Hofmann, A. et al., *Proc. Natl. Acad. Sci. USA* 93: 5185-5190 (1996)). As will be appreciated by those in the art, modifications of the system by pseudotyping allows use of retroviral vectors for all eukaryotic cells, particularly for higher eukaryotes (Morgan, R. A. et al., *J. Virol.* 67: 4712-4721 (1993); Yang, Y. et al., *Hum. Gene Ther.* 6:1203-1213 (1995)).

In addition, the expression vectors also contain a selectable marker gene to allow selection of transformed host cells. Generally, the selection will confer a detectable phenotype that enriches for cells containing the expression vector and further permits differentiation between cells that express and do not express the selection gene. Selection genes are well known in the art and will vary with the host cell used. Suitable selection genes included genes that render the cell resistant to a drug, genes that permit growth in nutritionally deficient media, and reporter genes (e.g., β-galactosidase, fluorescent proteins, glucouronidase, etc.), all of which are well known in the art and available to the skilled artisan.

There are a variety of techniques available for introducing nucleic acids into viable cells. By "introduced" into herein is meant that the nucleic acid enters the cells in a manner suitable for subsequent expression of the nucleic acid. Techniques for introducing the nucleic acids will vary depending on whether the nucleic acid is transferred in vitro into cultured cells or in vivo into the cells of the intended host organism and the type of host organism. Exemplary for introducing the nucleic acids in vitro include the use of liposomes, Lipofectin®, electroporation, microinjection, cell fusion, DEAE dextran, calcium phosphate precipitation, and biolistic particle bombardment. Techniques for transfer in vivo include direct introduction of the nucleic acid, use of viral vectors, typically retroviral vectors, and liposome mediated transfection, such as viral coated liposome mediated transfection. The nucleic acids expressing the peptides of the present invention may exist transiently or stably in the cytoplasm or stably integrate into the chromosome of the host (i.e., through use of standard regulatory sequences, selection markers, etc.). Suitable selection genes and marker genes are used in the expression vectors of the present invention.

In some situations, it is desirable to include an agent that targets the target cells or tissues, such as an antibody specific for a cell surface protein or the target cell, a ligand for a receptor on the target cell, a lipid component on the cell membrane, or a carbohydrate on the cell surface. If liposomes are employed, proteins that bind a cell surface protein which is endocytosed may be used for targeting and/or facilitating uptake. These include as non-limiting examples, capsid proteins or fragments thereof tropic for a particular cell types, antibodies for proteins which undergo internalization (Wu, G. Y. et al., *J. Biol. Chem.* 262: 4429-4432 (1987); Wagner, E. et al., *Proc. Natl. Aced. Sci. USA* 87: 3410-3414 (1990)), or enhance in vivo half-life.

Expression is done in a wide range of host cells that span prokaryotes and eukaryotes, including bacteria, yeast, plants, insects, and animals. The oligopeptides of the present invention may be expressed in, among others, *E. coli., Saccharomyces cerevisiae, Saccharomyces pombe*, Tobacco or *Arabidopsis* plants, insect *Schneider* cells, and mammalian cells, such as COS, CHO, HeLa, and the like, either intracellularly or in a secreted form by fusing the peptides to an appropriate signal peptide. Secretion from the host cell may be done by fusing the DNA encoding the oligopeptide and a DNA encoding a signal peptide. Secretory signals are well known in the art for bacteria, yeast, insects, plants, and mammalian systems. Nucleic acids expressing the oligopeptides may be inserted into cells, for example stem cells for tissue expression or bacteria for gut expression, and the cells transplanted into the host to provide an in vivo source of the oligopeptides.

6.6 Purified Peptides

In a preferred embodiment, the oligopeptides of the present invention may be purified or isolated after synthesis or expression. By "purified" or "isolated" is meant free from the environment in which the peptide is synthesized or expressed and in a form where it can be practically used. Thus purified or isolated is meant that the peptide or its derivative is substantially pure, i.e., more than 90% pure, preferably more than 95% pure, and preferably more than 99% pure. The oligopeptides and derivatives thereof may be purified and isolated by way known to those skilled in the art, depending on other components present in the sample. Standard purification methods include electrophoretic, immunological, and chromatographic techniques, including ion exchange, hydrophobic, affinity, size exclusion, reverse phase HPLC, and chromatofocusing. The proteins may also be purified by selective solubility, for instance in the presence of salts or organic solvents. The degree of purification necessary will vary depending on use of the subject oligopeptides. Thus, in some instances no purification will be necessary.

For the most part, the compositions used will comprise at least 20% by weight of the desired product, more usually at least about 75% by weight, preferably at least about 95% by weight, and usually at least about 99.5% by weight, relative to contaminants related to the method of product preparation, the purification procedure, and its intended use, for example with a pharmaceutical carrier for the purposes of therapeutic treatment. Usually, the percentages will be based upon total protein.

6.7 Pharmaceutical Compositions

The subject compositions, either alone or in combination, may be used in vitro, ex vivo, and in vivo depending on the particular application. In accordance, the present invention provides for administering a pharmaceutical composition comprising a pharmaceutically acceptable carrier and a pharmacologically effective amount of one or more of the subject peptides, or suitable salts thereof. The pharmaceutical composition may be formulated as powders, granules, solutions, suspensions, aerosols, solids, pills, tablets, capsules, gels, topical crimes, suppositories, transdermal patches (e.g., via transdermal iontophoresis), etc.

As indicated above, pharmaceutically acceptable salts of the peptides is intended to include any art recognized pharmaceutically acceptable salts including organic and inorganic acids and/or bases. Examples of salts include sodium, potassium, lithium, ammonium, calcium, as well as primary, secondary, and tertiary amines, esters of lower hydrocarbons, such as methyl, ethyl, and propyl. Other salts include organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any of standard pharmaceutically accepted carriers known to those of ordinary skill in the art in formulating pharmaceutical compositions. Thus, the subject peptides, by themselves, such as being present as pharmaceutically acceptable salts, or as conjugates, or nucleic acid vehicles encoding such peptides, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients. The formulations may include bactericidal agents, stabilizers, buffers, emulsifiers, preservatives, sweetening agents, lubricants, or the like. If administration is by oral route, the oligopeptides may be protected from degradation by using a suitable enteric coating, or by other suitable protective means, for example internment in a polymer matrix such as microparticles or pH sensitive hydrogels.

Suitable formulations may be found in, among others, Remington's Pharmaceutical Sciences, Mack Publishing Co., Philadelphia, Pa. (17th ed., 1985) and Handbook of Pharmceutical Excipients, 3rd Ed, Washington D.C., American Pharmaceutical Association (Kibbe, A. H. ed., 2000); hereby incorporated by reference in their entirety. The pharmaceutical compositions described herein can be made in a manner well known to those skilled in the art (e.g., by means conventional in the art, including, by way of example and not limitation, mixing, dissolving, granulating, levigating, emulsifying, encapsulating, entrapping or lyophilizing processes).

Additionally, the peptides may also be introduced or encapsulated into the lumen of liposomes for delivery and for extending life time of the peptides ex vivo or in vivo. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids (see, e.g., U.S. Pat. No. 5,833,948).

Cationic lipids are also suitable for forming liposomes. Generally, the cationic lipids have a net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecydoxy)propyl]-N,N-dimethyl-N-N-hydroxyethylammonium bromide; N-[1-(2,3-dioleyloxy)propyl]-N,N-dimethyl-N-hydroxy ethylammonium bromide; N-[1-(2,3-dioleyloxy) propyl]-N,N,N-trimethylammonium chloride; 3-[N-(N',N'-dimethylaminoethane) carbamoyl]cholesterol; and dimethyidioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH (see, e.g., U.S. Pat. Nos. 4,789,633 and 4,873,089). Generally, pH sensitive liposomes are acid sensitive. Thus, fusion is enhanced in physiological environments where the pH is mildly acidic, for example the environment of a lysosome, endosome and inflammatory tissues. This property allows direct release of the liposome contents into the intracellular environment following endocytosis of liposomes (Mizoue, T., *Int J. Pharm.* 237:129-137 (2002)).

Another form of fusogenic liposomes comprises liposomes that contain a fusion enhancing agent. That is, when incorporated into the liposome or attached to the lipids, the agents enhance fusion of the liposome with other cellular membranes, thus resulting in delivery of the liposome contents into the cell. The agents may be fusion enhancing peptides or proteins, including hemaggulutinin HA2 of influenza virus (Schoen, P., *Gene Ther.* 6: 823-832 (1999)); Sendai virus envelope glycoproteins (Mizuguchi, H., *Biochem. Biophys. Res. Commun.* 218: 402-407 (1996)); vesicular stomatitis virus envelope glycoproteins (VSV-G) glycoprotein (Abe, A. et al., *J Virol.* 72: 6159-63 (1998)); peptide segments or mimics of fusion enhancing proteins; and synthetic fusion enhancing peptides (Kono, K. et al., *Biochim. Biophys. Acta.* 1164: 81-90 (1993); Pecheur, E. I., *Biochemistry* 37: 2361-71 (1998); U.S. Pat. No. 6,372,720).

Liposomes also include vesicles derivatized with a hydrophilic polymer, as provided in U.S. Pat. Nos. 5,013,556 and 5,395,619, hereby incorporated by reference, (see also, Kono, K. et al., *J. Controlled Release* 68: 225-35 (2000); Zalipsky, S. et al., *Bioconjug. Chem.* 6: 705-708 (1995)) to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization (see Wu et al., supra; Wagner et al., supra), may be used for targeting and/or facilitating uptake of the liposomes to specific cells or tissues.

Liposomes are prepared by ways well known in the art (see for example, Szoka, F. et al., *Ann. Rev. Biophys. Bioeng.* 9: 467-508 (1980)). One typical method is the lipid film hydration technique in which lipid components are mixed in an organic solvent followed by evaporation of the solvent to generate a lipid film. Hydration of the film in aqueous buffer solution, preferably containing the subject peptide or nucleic acid, results in an emulsion, which is sonicated or extruded to reduce the size and polydispersity. Other methods include reverse-phase evaporation (see, e.g., Pidgeon, C. et al., *Biochemistry* 26: 17-29 (1987); Duzgunes, N. et al., *Biochim. Biophys. Acta.* 732: 289-99 (1983)), freezing and thawing of phospholipid mixtures, and ether infusion.

In another preferred embodiment, the carriers are in the form of microparticles, microcapsules, micropheres and nanoparticles, which may be biodegradable or non-biodegradable (see, e.g., *Microencapsulates: Methods and Industral Applications*, in Drugs and Pharmaceutical Sciences, Vol 73, Marcel Dekker Inc., New York (Benita, S. ed, 1996); incorporated by reference). As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. As used herein, microparticles have a particle size range of about 1 to about >1000 microns. Nanoparticles have a particle size range of about 10 to about 1000 nm.

A variety of materials are useful for making microparticles. Non-biodegradable microcapsules and microparticles include, but not limited to, those made of polysulfones, poly (acrylonitrile-co-vinyl chloride), ethylene-vinyl acetate, hydroxyethylmethacrylate-methyl-methacrylate copolymers. These are useful for Implantation purposes where the encapsulated peptide diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly($\beta$-hydroxybutyrate)), poly ($\gamma$-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see, e.g., U.S. Pat. No. 4,389,330); emulsification and evaporation (Maysinger, D. et al., *Exp. Neuro.* 141: 47-56 (1996); Jeffrey, H. et al., *Pharm. Res.* 10: 362-68 (1993)), spray drying, and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are limited to, poly(lactic acid) (PLA; see Zambaux et al., *J. Control Release* 60: 179-188 (1999)), poly(lactide-co-glycolide), blends of poly(lactide-co-glycolide) and polycarprolactone, diblock polymer poly(l-leucine-block-l-glutamate), diblock and triblock poly(lactic acid) (PLA) and poly(ethylene oxide) (PEO) (De Jaeghere, F. et al., *Pharm. Dev. Technol.;* 5: 473-83 (2000)), acrylates, arylamides, polystyrene, and the like. As described for microparticles, nanoparticles may be non-biodegradable or biodegradable. Nanoparticles may be also be made from poly(alkylcyanoacrylate), for example poly(butylcyanoacrylate), in which the peptide is absorbed onto the nanoparticles and coated with surfactants (e.g., polysorbate 80). Methods for making nanoparticles are similar to those for making microparticles and include, among others, emulsion polymerization in continuous aqueous phase, emulsification-evaporation, solvent displacement, and emulsification-diffusion techniques (see Kreuter, J. *Nano-particle Preparation and Applications*, in Microcapsules and nanoparticles in medicine and pharmacy, pg. 125-148, (M. Donbrow, ed.) CRC Press, Boca Rotan, Fla. (1991); incorporated by reference).

Hydrogels are also useful in delivering the subject agents into a host. Generally, hydrogels are crosslinked, hydrophilic polymer networks permeable to a wide variety of drug compounds, including peptides. Hydrogels have the advantage of selective trigger of polymer swelling, which results in controlled release of the entrapped drug compound. Depending on the composition of the polymer network, swelling and subsequent release may be triggered by a variety of stimuli, including pH, ionic strength, thermal, electrical, ultrasound, and enzyme activities. Non-limiting examples of polymers useful in hydrogel compositions include, among others, those formed from polymers of poly(lactide- co-glycolide), poly (N-isopropylacrylamide); poly(methacrylic acid-g-polyethylene glycol); polyacrylic acid and poly(oxypropylene-co-oxyethylene) glycol; and natural compounds such as chrondroitan sulfate, chitosan, gelatin, fibrinogen, or mixtures of synthetic and natural polymers, for example chitosan-poly(ethylene oxide). The polymers are crosslinked reversibly or irreversibly to form gels embedded with the oligopeptides of the present invention (see, e.g., U.S. Pat. Nos. 6,451,346; 6,410,645; 6,432,440; 6,395,299; 6,361,797; 6,333,194; 6,297,337; Johnson, O. et al., *Nature Med.* 2: 795 (1996); incorporated by reference in their entirety).

6.8 Dose and Administration

The concentrations of the peptides or nucleic acid encoding therefore will be determined empirically in accordance with conventional procedures for the particular purpose. Generally, for administering the peptides ex vivo or in vivo for therapeutic purposes, the subject peptides are given at a pharmacologically effective dose. By "pharmacologically effective amount" or "pharmacologically effective dose" is an amount sufficient to produce the desired physiological effect or amount capable of achieving the desired result, particularly for treating the disorder or disease condition, including reducing or eliminating one or more symptoms or manifestations of the disorder or disease.

The amount administered to the host will vary depending upon what is being administered, the purpose of the administration, such as prophylaxis or therapy, the state of the host, the manner of administration, the number of administrations, interval between administrations, and the like. These can be determined empirically by those skilled in the art and may be adjusted for the extent of the therapeutic response. Factors to consider in determining an appropriate dose include, but is not limited to, size and weight of the subject, the age and sex of the subject, the severity of the symptom, the stage of the disease, method of delivery of the agent, half-life of the agents, and efficacy of the agents. Stage of the disease to consider includes whether the disease is acute or chronic, relapsing or remitting phase, and the progressiveness of the disease. Determining the dosages and times of administration for a therapeutically effective amount are well within the skill of the ordinary person in the art.

For any compounds used in the present invention, therapeutically effective dose is readily determined by methods well known in the art. For example, an initial effective dose can be estimated initially from cell culture assays. An indicator of inflammatory response or indicator of peptide activity may be used, such as expression levels of pro-inflammatory cytokines (e.g., TNF-$\alpha$, IFN-$\gamma$, IL-6, IL-12, etc.), inhibition of CTL activity, presence of IC disease markers (e.g., histamine, Substance P, etc). A dose can then be formulated in animal models to generate a circulating concentration or tissue concentration, including that of the $IC_{50}$ as determined by the cell culture assays.

In addition, the toxicity and therapeutic efficacy are generally determined by cell culture assays and/or experimental animals, typically by determining a $LD_{50}$ (lethal dose to 50% of the test population) and $ED_{50}$ (therapeutically effectiveness in 50% of the test population). The dose ratio of toxicity and therapeutic effectiveness is the therapeutic index. Preferred are compositions, individually or in combination, exhibiting high therapeutic indices. Determination of the effective amount is well within the skill of those in the art, particularly given the detailed disclosure provided herein.

Generally, in the case where a peptide composition is administered directly to a host, the present invention provides for a bolus or infusion of the subject composition that will administered in the range of about 0.01-50, more usually from about 0.1-25 mg/kg body weight of host. The amount will generally be adjusted depending upon the half-life of the peptide, where the half-life will generally be at least one minute, more usually at least about 10 min, desirably in the range of about 10 min to 12 h. Short half-lives are acceptable, so long as efficacy can be achieved with individual dosages, continuous infusion, or repetitive dosages. Formulations for administration may be presented in unit a dosage form, e.g., in ampules, capsules, pills, or in multidose containers or injectables. Dosages in the lower portion of the range and even lower dosages may be employed, where the peptide has an enhanced half-life or is provided as a depot, such as a slow release composition comprising particles, a polymer matrix which maintains the peptide over an extended period of time (e.g., a collagen matrix, carbomer, etc.), use of a pump which continuously infuses the peptide over an extended period of time with a substantially continuous rate, or the like. The dose is also adjusted in relation to the route of administration. Thus for example, if the administration is systemic, either oral or intravenous, the dose is appropriately adjusted for bioavailability. The host or subject may be any mammal including domestic animals, pets, laboratory animals, primates, particularly human subjects.

In addition to administering the subject peptide compositions directly to a cell culture in vitro, to particular cells ex vivo, or to a mammalian host in vivo, nucleic acid molecules (DNA or RNA) encoding the subject peptides may also be administered thereto, thereby providing an effective source of the subject peptides for the application desired. As described above, nucleic acid molecules encoding the subject peptides may be cloned into any of a number of well known expression plasmids (Sambrook et al., supra) and/or viral vectors, preferably adenoviral or retroviral vectors (see for example, Jacobs et al., *J. Virol.* 66:2086-2095 (1992), Lowenstein, *Bio/Technology* 12:1075-1079 (1994) and Berkner, *Biotechniques* 6:616-624 (1988)), under the transcriptional regulation of control sequences which function to promote expression of the nucleic acid in the appropriate environment. Such nucleic acid-based vehicles may be administered directly to the cells or tissues ex vivo (e.g., ex vivo viral infection of cells for transplant of peptide producing cells) or to a desired site in vivo, e.g. by injection, catheter, orally (e.g., hydrogels), and the like, or, in the case of viral-based vectors, by systemic administration. Tissue specific promoters may optionally be employed, assuring that the peptide of interest is expressed only in a particular tissue or cell type of choice. Methods for recombinantly preparing such nucleic acid-based vehicles are well known in the art, as are techniques for administering nucleic acid-based vehicles for peptide production.

For the purposes of this invention, the methods of administration are chosen depending on the condition being treated, the form of the subject peptide, and the pharmaceutical composition. Administration of the oligopeptides can be done in a variety of ways, including, but not limited to, cutaneously, subcutaneously, intravenously, orally, topically, transdermally, intraperitoneally, intramuscularly, and intravesically. For example, microparticle, microsphere, and microencapsulate formulations are useful for oral, intramuscular, or subcutaneous administrations. Liposomes and nanoparticles are additionally suitable for intravenous administrations. Administration of the pharmaceutical compositions may be through a single route or concurrently by several routes. For instance, oral administration can be accompanied by intravenous or parenteral injections.

In one preferred embodiment, the method of administration is by oral delivery, in the form of a powder, tablet, pill, or capsule. Pharmaceutical formulations for oral administration may be made by combining one or more peptide with suitable excipients, such as sugars (e.g., lactose, sucrose, mannitol, or sorbitol), cellulose (e.g., starch, methyl cellulose, hydroxymethyl cellulose, carboxymethyl cellulose, etc.), gelatin, glycine, saccharin, magnesium carbonate, calcium carbonate, polymers such as polyethylene glycol or polyvinylpyrrolidone, and the like. The pills, tablets, or capsules may have an enteric coating, which remains intact in the stomach but dissolves in the intestine. Various enteric coating are known in the art, a number of which are commercially available, including, but not limited to, methacrylic acid-methacrylic acid ester copolymers, polymer cellulose ether, cellulose acetate phthalate, polyvinyl acetate phthalate, hydroxypropyl methyl cellulose phthalate, and the like. Alternatively, oral formulations of the peptides are in prepared in a suitable diluent. Suitable diluents include various liquid form (e.g., syrups, slurries, suspensions, etc.) in aqueous diluents such as water, saline, phosphate buffered saline, aqueous ethanol, solutions of sugars (e.g. sucrose, mannitol, or sorbitol), glycerol, aqueous suspensions of gelatin, methyl cellulose, hydroxylmethyl cellulose, cyclodextrins, and the like. In some embodiments, lipohilic solvents are used, including oils, for instance, vegetable oils, peanut oil, sesame oil, olive oil, corn oil, safflower oil, soybean oil, etc.; fatty acid esters, such as oleates, triglycerides, etc.; cholesterol derivatives, including cholesterol oleate, cholesterol linoleate, cholesterol myristilate, etc.; liposomes; and the like.

In yet another preferred embodiment, the administration is carried out cutaneously, subcutaneously, intraperitonealy, intramuscularly and intravenously. As discussed above, these are in the form of peptides dissolved or suspended in suitable aqueous medium. Additionally, the pharmaceutical compositions for injection may be prepared in lipophilic solvents, which include, but is not limited to, oils, such as vegetable oils, olive oil, peanut oil, palm oil soybean oil, safflower oil, etc; synthetic fatty acid esters, such as ethyl oleate or triglycerides; cholesterol derivatives, including cholesterol oleate, cholesterol linoleate, cholesterol myristilate, etc.; or liposomes, as described above. The compositions may be prepared directly in the lipophilic solvent or preferably, as water emulsions, (see for example, Liu, F. et al., *Pharm. Res.* 12: 1060-1064 (1995); Prankerd, R. J. *J. Parent. Sci. Tech.* 44: 13949 (1990); and U.S. Pat. No. 5,651,991).

In a particularly preferred embodiment, the subject compositions are administered by intravesical instillation. The procedure generally involves inserting a catheter into urinary tract and filling the bladder with a suitable diluent containing the subject composition. Filling may be made by manual infusion or renal pump. Electromotive drug administration can further assist intravesical drug delivery (see for example, Riedl, C. R. et al., *J. Endourol.* 12: 269-72 (1998); incorporated by reference).

The delivery systems also include sustained release or long-term delivery methods, which are well known to those skilled in the art. By "sustained release or" "long term release" as used herein is meant that the delivery system administers a pharmaceutically therapeutic amount of subject compounds for more than a day, preferably more than a week, and most preferable at least about 30 days to 60 days, or longer. Long term release systems may comprise implantable solids or gels containing the subject peptide, such as biodegradable polymers described above (Brown, D. M. et al., *Anticancer Drugs* 7: 507-513 (1996)); pumps, including peristaltic pumps and fluorocarbon propellant pumps; osmotic and mini-osmotic pumps; and the like. Peristaltic pumps deliver a set amount of drug with each activation of the pump, and the reservoir can be refilled, preferably percutaneously through a port. A controller sets the dosage and can also provides a readout on dosage delivered, dosage remaining, and frequency of delivery. Fluorocarbon propellant pumps utilize a fluorocarbon liquid to operate the pump. The fluorocarbon liquid exerts a vapor pressure above atmospheric pressure and compresses a chamber containing the drug to release the drug. Osmotic pumps (and mini-osmotic pumps) utilize osmotic pressure to release the drug at a constant rate. The peptide compositions are contained in an impermeable diaphragm, which is surrounded by the osmotic agent. A semipermeable membrane contains the osmotic agent, and the entire pump is housed in a casing. Diffusion of water through the semipermeable membrane squeezes the diaphragm holding the drug, forcing the drug into bloodstream, organ, or tissue. These and other such implants are particularly useful in treating a condition manifesting recurring episodes or which are progressive in nature, by delivering the oligopeptides of the invention via systemic (e.g., intravenous or subcutaneous) or localized doses in a sustained, long term manner.

The present invention also encompasses the oligopeptides in the form of a kit or packaged formulation. A kit or packaged drug as used herein includes one or more dosages of a pharmaceutical composition comprising one or more of the oligopepuides, and salts thereof, in a container holding the dosages for administration to treat the particular disorder or disease condition. For example, the package may contain the peptides along with a pharmaceutical carrier combined in the form of a powder for mixing in an aqueous solution, which can be injected or administered intravesically. The package or kit includes appropriate instructions, which encompasses diagrams, recordings (e.g., audio, video, compact disc), and computer programs providing directions for use of the formulation.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching.

All publications and patent applications mentioned in this specification are herein incorporated by reference to the same extent as if each individual publication or patent application was specifically and individually indicated to be incorporated by reference.

7. EXAMPLES

7.1 Example 1

Effect of RDP58 Oligopeptide on Cytokine Production in Bladder Cells

The ability of RDP58 peptide bc-1nL in inhibiting cytokine production in bladder cells was examined. In a first study, BALB/c mice were euthanized with $CO_2$ and the bladders harvested after voiding it of urine. Bladders were gently washed with RMPI 1640 media containing penicillin and streptomycin and minced into 1-2 mm pieces. Equal amounts of tissue were incubated overnight at 37° C. in 0.5 ml of RPMI culture medium in the presence of 1 ug LPS (*E. coli.* 055:B5; Sigma), 50 ul of RDP58 peptide (1 mg/ml) (50 uM final concentration), 1 ug LPS+50 ul of RDP58 peptde, or media alone. The culture supernatants were collected after 18 hrs, clarified by centrifugation, and assayed by ELISA for cytokines TNF-α and IFN-γ.

The presence of RDP58 peptide inhibited TNF-α production by about 30% in each pool. Similarly, RDP58 peptide inhibited IFN-γ production by about 10% in one pool and by 67% in the second. Thus, the results show that the RDP58 peptide was effective in inhibiting cytokine production in bladder cells.

In a second study, bladders from 12 normal mice were harvested, pooled into four sets of three bladders, and the tissues minced into 1-2 mm pieces. Equal amounts of tissue were incubated overnight in culture media containing LPS, RDP58 peptide, LPS+RDP58 peptide, or media, as described above. After clarifying the culture medium by centrifugation, supernatants were assayed for presence of TNF-α by ELISA.

The results show that the presence of RDP58 peptide inhibited TNF-α production to about 3.9-13% of the levels seen with LPS alone, with an average of 9.8%±4.1% (p<0.001) of that in LPS stimulated pools (Table V). Thus, the RDP58 peptide consistently and effectively inhibited TNF-α production in bladder cells.

TABLE V

TNF-α Levels[a] in LPS Treated Bladder Cells

|  | Control | LPS | RDP58 | RDP58/ LPS | % of LPS Induced Levels[b] |
|---|---|---|---|---|---|
| Pool 1 | 0 | 473.1 | 0 | 49.6 | 10.5 |
| Pool 2 | 53.6 | 444.6 | 17.1 | 52.6 | 11.8 |
| Pool 3 | 0 | 361.1 | 0 | 47.1 | 13.0 |
| Pool 4 | 0 | 431.1 | 10.6 | 16.6 | 3.9 |
| Average | 13.4 | 427.5 | 6.9 | 41.5 | 9.8 |
| Stand. Dev. | 26.8 | 47.6 | 8.4 | 16.7 | 4.1 |

[a] TNF-α levels in pg/ml
[b] % TNF-α levels in RDP58/LPS treated samples relative to LPS only treated samples

7.2 Example 2

Acute Interstitial Cystitis Model

Induction of Acute Interstitial Cystitis

Acute IC model was induced by transurethrally catheterizing mice and instilling with 15 ug of *E.coli*. lipopolysaccharide (LPS) in 150 ul. Controls were instilled with 150 ul of saline. After 45 min, bladders were drained, and 150 ul of either distilled water (DW) or RDP58 (1 mg/ml) was instilled for 30 min. Four hours after final treatment, bladders were excised (n=3 per group) for analysis.

Assays for Cytokines, Nerve Growth Factor, and Substance P

Excised bladders were washed briefly in PBS and then transferred to 500 ul of RPMI/Pen/Strep media containing 10% FBS. With sterile surgical scissors, bladders were sliced into 1 mm sections and left overnight in the RPMI media (16 hrs) at 37° C. with 5% $CO_2$. After incubation, the samples were collected into centrifuge tubes and spun down at ~3000 rpm to remove bladder slices and debris. The supernatant was frozen at −70° C. until analyzed by ELISA. Assays for Substance P used a kit from Assay Designs, Inc. (Cat. No. 900-018). Assays for NGF used a sandwich ELISA system from Chemicon international (Cat. No. CYT304). Assays for cytokines TNF-α, IFN-γ, and IL-6 used ELISA kits from Biosource (Camarillo, Calif.: TNF-α Immunoassay Cat. No. KMC3011C; IL-6 Immunoassay Cat. No. KMC0061C; and IFN-γ Immunoassay Cat No. KM4021C).

Histamine Assay

Assay for histamine used a HTRF Bioassay Kit (CIS blo international, France). In the assay, histamine in the sample competes with a labelled conjugate of histamine, preventing labelled anti-histamine antibodies from binding to the conjugate, thereby reducing FRET between the labels on the conjugate and the antibody. In vitro assays for histamine release used rat basophil cell line RBL-2H3.

Measuring Bladder Permeability

Bladder permeability was determined by inducing acute cystitis by transurethrally catheterizing mice and instilling 15 ug of LPS in 150 ul volume. Controls were instilled with 150 ul of saline. After 45 min, bladders were drained and 150 ul of FITC-dextran (25 mg/ml) instilled for 30 min. FITC-dextran is a polymer of anhydroglucose composed of 95% alpha-D linkages, with FITC fluors conjugated randomly to hydroxyl groups. It does not appreciably bind to plasma proteins and is stable in vivo for more than 24 hrs.

Following FITC-dextran instillation, blood was collected by cardiac draw and serum obtained by centrifugation for 5 min at 4,000 rpm. Fluorescence of the serum was measured at 485 nm/535 nm. When determining the effect of RDP58 oligopeptide on bladder permeability, animals were instilled with saline for control groups, and saline or RDP58 for LPS induced animals. Naive animals, which had not received either saline or LPS, were left untreated.

7.3 Example 3

Chronic Interstitial Cystitis Model

Induction of Chronic Interstitial Cystitis

Chronic IC model was induced in mice by transurethrally catheterizing mice and instilling with 15 ug of *E.coli.* lipopolysaccharide (LPS) in 150 ul. Controls were instilled with 150 ul of saline. Animals were treated three times per week for two weeks. To determine the effect of RDP58, animals were instilled with the peptide following 14 days of LPS instillation. Histological analyses of the bladders were carried out 24 or 72 hrs post treatment. Cytokine levels were assayed by removing the bladder 24 hrs following RDP58 treatment, culturing the tissue ex vivo, and assaying for cytokines, as described above. Bladder permeability used the FITC-dextran assay.

Histological Analysis of Tissue

Bladder from the various animal groups were removed after the treatments and then sectioned. Morphology was examined by staining with haematoxylin-eosin. Sections were examined for the presence of T-cell differentiation markers CD3 or CD45 by immunostaining with anti-CD45 and anti-CD3 antibodies.

What is claimed:

1. A method of therapeutically treating interstitial cystitis ("IC"), comprising: administering to an interstitial cystitis-afflicted subject a pharmaceutically effective amount of a composition comprising an oligopeptide, wherein said oligopeptide comprises the amino acid sequence set forth as SEQ ID NO:28.

2. The method of claim 1, wherein the oligopeptide consists of the amino acid sequence set forth as SEQ ID NO:28.

3. The method of claim 1, wherein at least one of the terminal amino acids is a modified amino acid.

4. The method of claim 3, wherein the modified amino acid is an amidated amino acid or salts thereof 5. The method of claim 1, wherein one or more of the amino acids of the oligopeptide are D isomers.

6. The method of claim 5, wherein all the amino acids of the oligopeptide, other than glycine, are the D-isomer.

7. The method of claim 1, wherein administering is by intravesicle instillation.

8. A method of treating interstitial cystitis, comprising contacting tissue or cells affected by IC with a pharmaceutically effective amount of a composition comprising an oligopeptide, wherein said oligopeptide comprises the amino acid sequence set forth as SEQ ID NO:28 to ameliorate a manifestation of interstitial cystitis.

9. The method of claim 8, wherein the manifestation is histamine release and the cells are mast cells.

10. The method of claim 8, wherein the manifestation is Substance P expression.

11. The method of claim 8, wherein the manifestation is degradation of urine/blood barrier.

12. The method of claim 8, wherein the oligopeptide consists of the amino acid sequence set forth as SEQ ID NO:28.

13. The method of claim 8, wherein one or more of the amino acids of the oligopeptide are the D-isomer.

14. The method of claim 13, wherein all the amino acids of the oligopeptide, other than glycine, are the D-isomer.

15. The method of claim 8, wherein at least one terminal amino acid residue is a modified amino acid.

16. The method of claim 15, wherein the modified amino acid is an amidated amino acid or salts thereof.

* * * * *